(12) United States Patent
Hiyoshi et al.

(10) Patent No.: US 12,268,715 B2
(45) Date of Patent: Apr. 8, 2025

(54) METHOD FOR PRODUCING BIOLOGICAL TISSUE-LIKE STRUCTURE

(71) Applicant: Orizuru Therapeutics, Inc., Fujisawa (JP)

(72) Inventors: Hideyuki Hiyoshi, Kanagawa (JP); Taisuke Mochida, Kanagawa (JP); Noriko Yamazoe, Kanagawa (JP); Junji Yamaura, Kanagawa (JP); Taro Toyoda, Kyoto (JP); Shuhei Konagaya, Kyoto (JP)

(73) Assignee: Orizuru Therapeutics, Inc., Kanagawa (JP)

( * ) Notice: Subject to any disclaimer, the term of this patent is extended or adjusted under 35 U.S.C. 154(b) by 749 days.

(21) Appl. No.: 17/602,421

(22) PCT Filed: Apr. 9, 2020

(86) PCT No.: PCT/JP2020/016642
§ 371 (c)(1),
(2) Date: Oct. 8, 2021

(87) PCT Pub. No.: WO2020/209389
PCT Pub. Date: Oct. 15, 2020

(65) Prior Publication Data
US 2022/0168357 A1    Jun. 2, 2022

(30) Foreign Application Priority Data

Apr. 10, 2019  (JP) ................. 2019-075100

(51) Int. Cl.
*C12N 5/074* (2010.01)
*A61K 35/39* (2015.01)
(Continued)

(52) U.S. Cl.
CPC ............. *A61K 35/39* (2013.01); *A61P 3/10* (2018.01); *C12N 5/0677* (2013.01);
(Continued)

(58) Field of Classification Search
CPC .................................................. C12N 5/0607
See application file for complete search history.

(56) References Cited

U.S. PATENT DOCUMENTS

2010/0227399 A1  9/2010  Funaki et al.
2011/0177593 A1  7/2011  Funaki et al.
(Continued)

FOREIGN PATENT DOCUMENTS

CN   101716382 A   6/2010
CN   101778935 A   7/2010
(Continued)

OTHER PUBLICATIONS

Office Action and Search Report dated Jan. 19, 2024 in CN 202080041859.0, with English translation.
(Continued)

*Primary Examiner* — Rosanne Kosson
(74) *Attorney, Agent, or Firm* — Foley & Lardner LLP

(57) ABSTRACT

An object of the present invention is to provide a novel method for producing a biological tissue-like structure comprising differentiated cells induced from pluripotent stem cells, and the present invention provides a method of forming a biological tissue-like structure together with host-derived blood vessels and connective tissue by transplanting a composition in which cells derived from pluripotent stem cells are disposed to be dispersed in a biocompatible material to induce the differentiation of the cells.

20 Claims, 11 Drawing Sheets

(51) Int. Cl.
*A61P 3/10* (2006.01)
*C12N 5/071* (2010.01)
(52) U.S. Cl.
CPC ...... *C12N 2506/45* (2013.01); *C12N 2513/00* (2013.01); *C12N 2533/56* (2013.01)

(56) References Cited

U.S. PATENT DOCUMENTS

| | | | |
|---|---|---|---|
| 2018/0119106 | A1 | 5/2018 | Millman et al. |
| 2021/0254014 | A1 | 8/2021 | Yamazoe et al. |

FOREIGN PATENT DOCUMENTS

| | | | |
|---|---|---|---|
| CN | 101855337 | A | 10/2010 |
| CN | 104984398 | A | 10/2015 |
| CN | 112313327 | A | 2/2021 |
| WO | WO-2004/038004 | A2 | 5/2004 |
| WO | WO-2018/183194 | A1 | 10/2018 |
| WO | WO-2018/226648 | A1 | 12/2018 |

OTHER PUBLICATIONS

Cooper et al., "Xenotransplantation—the current status and prospects," British Medical Bulletin, Mar. 1, 2018, 125:5-14.

Fedunina et al., Cell-gene therapy of Type 1 diabetes, The production of insulin-producing cells from human multipotent stromal cells, LAP Lambert Academic Publishing, Mar. 14, 2012, 15-21, with English translation.

Korel et al., "Directed Reprogramming Somatic Cells: Advantages and disadvantages induced pluripotent stem cells (Literature Review)," Siberian Scientific Medical Journal, Apr. 2018, 21-26, with English translation.

Office Action dated Sep. 7, 2023 in RU 2021132424, with English translation.

Svanidze et al., "High hardness in the biocompatible intermetallic compound beta-T13-Au," Sci. Adv., Jul. 20, 2016, 2:e1600319, 1-6.

Bhang et al., "Mutual effect of subcutaneously transplanted human adipose-derived stem cells and pancreatic islets within fibrin gel," Biomaterials, Jul. 1, 2013, 34(30):7247-7256.

International Search Report dated Jun. 23, 2020 in PCT/JP2020/016642.

Kim et al., "Islet-like organoids derived from human pluripotent stem cells efficiently function in the glucose responsiveness in vitro and in vivo," Scientific Reports, Oct. 12, 2016, 6(35145):1-13.

Rezania et al., "Reversal of diabetes with insulin-producing cells derived in vitro from human pluripotent stem cells," Nature Biotechnology, Sep. 11, 2014, 32(11):1121-1133.

Riopel et al., "Fibrin supports human fetal islet-epithelial cell differentiation via p70s6k and promotes vascular formation during transplantation," Laboratory Investigation, Jun. 1, 2015, 95:925-936.

Riopel et al., "Fibrin, a Scaffold Material for Islet Transplantation and Pancreatic Endocrine Tissue Engineering," Tissue Engineering: Part B, 2015 (online Jul. 23, 2014), 21(1):34-44.

Robert et al., "Functional Beta Cell Mass from Device-Encapsulated hESC-Derived Pancreatic Endoderm Achieving Metabolic Control," Stem Cell Reports, Mar. 13, 2018 (online Mar. 1, 2018), 10(3):739-750.

Song et al., "Economic 3D-printing approach for transplantation of human stem cell-derived Beta-like cells," Biofabrication, Dec. 1, 2016, 9(1):015002, 1-24.

Office Action with Search Report dated Jun. 19, 2024 in TW 109111993.

Supplementary European Search Report dated Dec. 8, 2022 in EP 20787264.9.

Office Action with Search Report dated May 31, 2024 in CN 202080041859.0, with English translation.

Zhang et al., Clinical Handbook of Tumor Markers, Jul. 31, 2008, 1:141, with partial English translation.

(A) Human C-peptide (pM)  (B) Blood glucose level (mg/dL)

Days after transplantation

Mean ± standard deviation for N = 3 or more, mean for N = 2

(A) Human C-peptide (pM)  (B) Glucose concentration in plasma (mg/dL)

Time after glucose loading (minutes)

Mean ± standard deviation for N = 3 or more, mean for N = 2

Mean + standard deviation (N = 3 to 8)

Mean + standard deviation (N = 3)

METHOD FOR PRODUCING BIOLOGICAL TISSUE-LIKE STRUCTURE

CROSS-REFERENCE TO RELATED APPLICATIONS

This application is the U.S. National Stage of PCT/JP2020/016642, filed Apr. 9, 2020, which claims priority to JP 2019-075100, filed Apr. 10, 2019.

TECHNICAL FIELD

The present invention relates to a biological tissue-like structure comprising differentiated cells derived from pluripotent stem cells, and a method for producing the biological tissue-like structure, and applications of the biological tissue-like structure.

BACKGROUND ART

Functional differentiated cells induced from pluripotent stem cells such as induced pluripotent cells and embryonic-stem cells (ES cells) are expected as a source of cells in transplantation and regenerative medicine. Currently, attempts to construct structures having functions comparative or similar to those of biological organs or tissues (hereinafter, referred to as "biological tissue-like structures") with the use of such functional differentiated cells have been made for transplantation treatment using tissue engineering. When producing a thick three-dimensional structure, however, it is difficult to supply oxygen, nutrients, and the like to all cells enough, thus keeping the cells viable in the structure is not easy both in vitro and in vivo. Due to such issues of thickness and size, conventional structures are often insufficient to exert functions comparable or similar to those of biological organs or tissues. A new approach that enables production of a thick three-dimensional biological tissue-like structure in a simple manner has been still desired in the art.

Research is underway to induce the differentiation of pluripotent stem cells such as induced pluripotent cells and embryonic-stem cells into endocrine cells that secrete hormones such as pancreatic β cells and pancreatic α cells and to apply the obtained cells to the treatment of diabetes mellitus. Approaches to produce endocrine cells by inducing the differentiation of pluripotent stem cells into pancreatic progenitor cells and transplanting the pancreatic progenitor cells in the living body and maturing the pancreatic progenitor cells have been reported. For example, Non Patent Literature 1 describes a method for producing endocrine cells comprising insulin-positive cells and glucagon-positive cells by transplanting pancreatic progenitor cells formed by inducing the differentiation of pluripotent stem cells into a mouse and maturing the pancreatic progenitor cells. However, no thick three-dimensional biological tissue-like structure that includes endocrine cells such as insulin-positive cells and glucagon-positive cells without ducts or cysts has been produced.

CITATION LIST

Non Patent Literature

Non Patent Literature 1: Robert T et al, Stem Cell Reports. 2018 Mar. 13; 10(3): 739-750.

SUMMARY OF INVENTION

Technical Problem

An object of the present invention is to provide a novel method for producing a biological tissue-like structure comprising differentiated cells induced from pluripotent stem cells.

Solution to Problem

The present inventors conducted diligent studies to attain the object and consequently found that by transplanting a composition comprising cells derived from pluripotent stem cells disposed to be dispersed in a biocompatible material into a biological tissue, the cells achieve graft survival and the differentiation thereof are induced to mature, and thus a biological tissue-like structure can be constructed together with host-derived blood vessels and connective tissue.

The present invention is based on these findings and encompasses the following inventions.

[1] A composition comprising: a biocompatible material to be used in a method for producing a biological tissue-like structure in a biological tissue of a host animal; and cells derived from human pluripotent stem cells, wherein the cells derived from human pluripotent stem cells are disposed to be dispersed in the biocompatible material.

[2] The composition according to [1], wherein the biocompatible material is a fibrin gel.

[3] The composition according to [2], wherein the fibrin gel is obtained by mixing the cells derived from human pluripotent stem cells with fibrinogen and thrombin for gelation immediately before use of the composition.

[4] The composition according to any of [1] to [3], wherein the cells derived from human pluripotent stem cells are present in a form of a plurality of spheroids.

[5] The composition according to any of [1] to [4], wherein a proportion of Ki67-positive cells in the cells derived from human pluripotent stem cells is less than 3%.

[6] The composition according to any of [1] to [5], wherein the cells derived from human pluripotent stem cells are insulin-producing cells.

[7] The composition according to any of [1] to [6], wherein the method comprises transplanting the composition into a biological tissue of a host animal to induce differentiation of the cells derived from human pluripotent stem cells disposed to be dispersed in the biocompatible material.

[8] The composition according to [7], wherein the biological tissue of the host animal is a subcutaneous tissue.

[9] The composition according to any of [1] to [8], wherein the biological tissue-like structure comprises: a plurality of clusters consisting of differentiated cells obtained by inducing differentiation of the cells derived from human pluripotent stem cells; a connective tissue derived from the host animal; and blood vessels derived from the host animal, wherein the plurality of clusters consisting of differentiated cells is present to be dispersed in the biological tissue-like structure, the connective tissue surrounds the plurality of clusters consisting of differentiated cells, and the blood vessels are intruding into the plurality of clusters consisting of differentiated cells.

[10] The composition according to [9], wherein the differentiated cells comprise no exocrine cell.

[11] A biological tissue-like structure comprising: a plurality of clusters consisting of differentiated cells obtained by inducing differentiation of cells derived from human pluripotent stem cells; a connective tissue derived from a host animal; and blood vessels derived from the host animal, wherein the plurality of clusters consisting of differentiated cells is present to be dispersed in the biological tissue-like structure, the connective tissue surrounds the plurality of clusters consisting of differentiated cells, and the blood vessels are intruding into the plurality of clusters consisting of differentiated cells.

[12] The biological tissue-like structure according to [11], wherein the differentiated cells comprise pancreatic β cells.

[12-A] The biological tissue-like structure according to [11], wherein the differentiated cells comprise pancreatic β cells and pancreatic α cells.

[13] The biological tissue-like structure according to any of [11] to [12-A], wherein the differentiated cells comprise no exocrine cell.

[14] The biological tissue-like structure according to any of [11] to [14], used for controlling a blood glucose level of a test subject with the biological tissue-like structure transplanted thereinto to a normal level.

[15] A method for producing a biological tissue-like structure, the method comprising transplanting a composition comprising a biocompatible material and cells derived from human pluripotent stem cells, wherein the cells derived from human pluripotent stem cells are disposed to be dispersed in the biocompatible material, into a biological tissue of a host animal to induce differentiation thereof.

[16] The method according to [15], wherein the biocompatible material is a fibrin gel.

[17] The method according to [16], wherein the fibrin gel is obtained by mixing the cells derived from human pluripotent stem cells with fibrinogen and thrombin for gelation immediately before use of the composition.

[18] The method according to any of [15] to [17], wherein the cells derived from human pluripotent stem cells are present in a form of a plurality of spheroids.

[19] The method according to any of [15] to [18], wherein a proportion of Ki67-positive cells in the cells derived from human pluripotent stem cells is less than 3%.

[20] The method according to any of [15] to [19], wherein the cells derived from human pluripotent stem cells are insulin-producing cells.

[21] The method according to any of [15] to [20], wherein the biological tissue of the host animal is a subcutaneous tissue.

[22] The method according to any of [15] to [21], wherein the biological tissue-like structure comprises: a plurality of clusters consisting of differentiated cells obtained by inducing differentiation of the dispersed cells derived from human pluripotent stem cells; a connective tissue derived from the host animal; and blood vessels derived from the host animal, wherein the plurality of clusters consisting of differentiated cells is present to be dispersed in the biological tissue-like structure, the connective tissue surrounds the plurality of clusters consisting of differentiated cells, and the blood vessels are intruding into the plurality of clusters consisting of differentiated cells.

[23] The method according to any of [15] to [22], wherein the differentiated cells comprise no exocrine cell.

The present specification encompasses the contents described in the specification and/or drawings of Japanese Patent Application No. 2019-075100 on which the priority of the present application is based.

All the publications, patents, and patent applications cited herein are totally incorporated herein by reference.

Advantageous Effects of Invention

The present invention can provide a novel method for producing a biological tissue-like structure comprising differentiated cells induced from pluripotent stem cells.

DESCRIPTION OF EMBODIMENTS

1. Terminology

Figure 1:
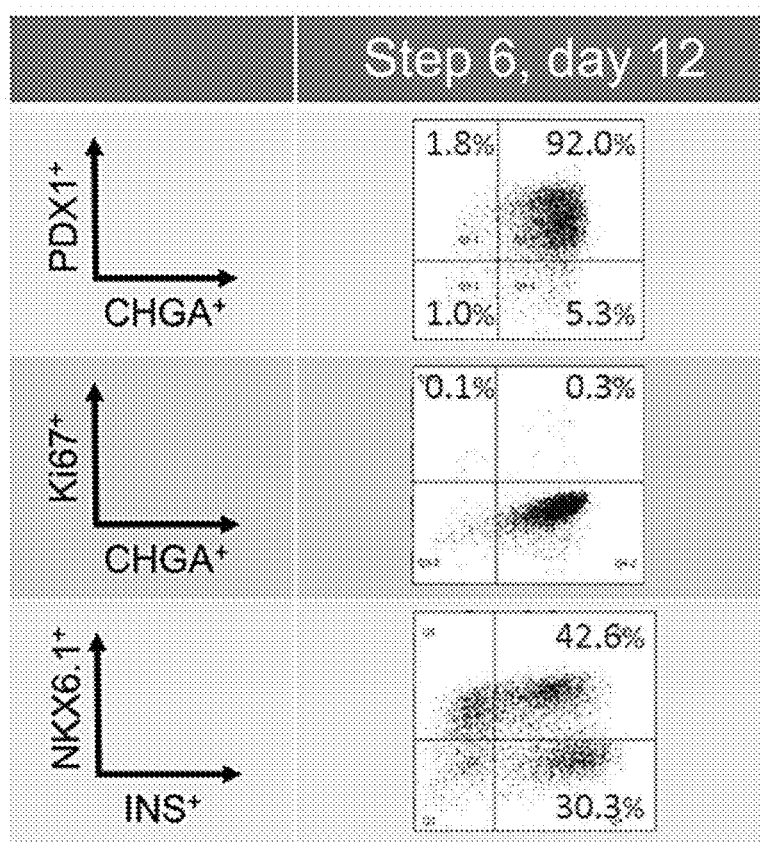
FIG. 1 shows results of analysis of protein expressions by flow cytometry for insulin-producing cells before transplantation.

As used herein, "about" refers to a value which may vary up to plus or minus 25%, 20%, 10%, 8%, 6%, 5%, 4%, 3%, 2%, or 1% from the reference value. Preferably, the term "about" or "around" refers to a range from minus or plus 15%, 10%, 5%, or 1% from the reference value.

As used herein, "comprise(s)" or "comprising" means inclusion of the element(s) following the word without limitation thereto. Accordingly, it indicates inclusion of the element(s) following the word, but does not indicate exclusion of any other element.

As used herein, "consist(s) of" or "consisting of" means inclusion of all the element(s) following the phrase and limitation thereto. Accordingly, the phrase "consist(s) of" or "consisting of" indicates that the enumerated element(s) is required or essential and substantially no other elements exist.

As used herein, "without the use of feeder cell(s)" means basically containing no feeder cells and using no medium preconditioned by culturing feeder cells. Accordingly, the medium does not contain any substance, such as a growth factor or a cytokine, secreted by feeder cells.

"Feeder cells" or "feeder" means cells that are co-cultured with another kind of cells, support the cells, and provide an environment that allows the cells to grow. The feeder cells may be derived from the same species as or a different species from the cells that they support. For example, as a feeder for human cells, human skin fibroblasts or human embryonic-stem cells may be used or a primary culture of murine embryonic fibroblasts or immortalized murine embryonic fibroblasts may be used. The feeder cells can be inactivated by exposure to radiation or treatment with mitomycin C.

As used herein, "adhered (adherent)" refers to cells are attached to a container, for example, cells are attached to a cell culture dish or a flask made of a sterilized plastic (or coated plastic) in the presence of an appropriate medium. Some cells cannot be maintained or grow in culture without adhering to the cell culture container. In contrast, non-adherent cells can be maintained and proliferate in culture without adhering to the container.

As used herein, "culture" refers to maintaining, growing, and/or differentiating cells in in vitro environment. "Culturing" means maintaining, proliferating (growing), and/or differentiating cells out of tissue or the living body, for example, in a cell culture dish or flask. The culture includes two-dimensional culture (plane culture) and three-dimensional culture (suspension culture).

As used herein, "enrich(es)" and "enrichment" refer to increasing the amount of a certain component in a composition such as a composition of cells and "enriched" refers, when used to describe a composition of cells, for example, a cell population, to a cell population increased in the amount of a certain component in comparison with the percentage of such component in the cell population before the enrichment. For example, a composition such as a cell population can be enriched for a target cell type and, accordingly, the percentage of the target cell type is increased in comparison with the percentage of the target cells present in the cell population before the enrichment. A cell population can be enriched for a target cell type by a method of selecting and sorting cells known in the art. A cell population can be enriched by a specific process of sorting or selection described herein. In a certain embodiment of the present invention, a cell population is enriched for a target cell population at least 20%, 30%, 40%, 50%, 60%, 70%, 80%, 85%, 90%, 95%, 97%, 98%, or 99% by a method of enriching the target cell population.

As used herein, "deplete(s)" and "depletion" refer to decreasing the amount of a certain component in cells or a composition such as a composition of cells and "depleted" refers, when used to describe cells or a composition of cells, for example, a cell population, to a cell population decreased in the amount of a certain component in comparison with the percentage of such component in the cell population before the depletion. For example, a composition such as a cell population can be depleted for a target cell type and, accordingly, the percentage of the target cell type is decreased in comparison with the percentage of the target cells present in the cell population before the depletion. A cell population can be depleted for a target cell type by a method of selecting and sorting cells known in the art. A cell population can be depleted by a specific process of sorting or selection described herein. In a certain embodiment of the present invention, a cell population is reduced (depleted) for a target cell population at least 50%, 80%, 85%, 90%, 95%, 97%, 98%, or 99% by a method of depleting a target cell population.

As used herein, "purify(ies)" and "purification" refer to removing impurities in a composition such as a composition of cells and making it pure for a certain component and "purified" refers, when used to describe a composition of cells, for example, a cell population, to a cell population in which the amount of impurities is decreased in comparison with the percentage of such components in the cell population before purification and the purity of a certain component is improved. For example, a composition such as a cell population can be purified for a target cell type and, accordingly, the percentage of the target cell type is increased in comparison with the percentage of the target cells present in the cell population before the purification. A cell population can be purified for a target cell type by a method of selecting and sorting cells known in the art. A cell population can be purified by a specific process of sorting or selection described herein. In a certain embodiment of the present invention, the purity of a target cell population is brought by a method of purifying a target cell population to at least 70%, 80%, 85%, 90%, 95%, 97%, 98%, or 99% or to the extent at which impurities (including contaminant cells) are undetectable.

As used herein, "factor having CDK8/19-inhibiting activity" means any substance having the inhibitory activity for CDK8/19. CDK8, in contrast to the other proteins of the same CDK family, is not required for cell proliferation. The inhibition of CDK8 has no great effect under usual conditions. CDK19 and CDK8 are similar to each other. Usually, the inhibition of CDK8 also involves the inhibition of CDK19.

"Growth factors" are endogenous proteins that promote differentiation and/or proliferation of particular cells. Examples of "growth factors" include epidermal growth factor (EGF), acid fibroblast growth factor (aFGF), basic fibroblast growth factor (bFGF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transformation growth factor beta (TGF-β), vascular endothelial growth factor (VEGF), transferrin, various interleukins (for example, IL-1 to IL-18), various colony-stimulating factors (for example, granulocyte/macrophage colony-stimulating factor (GM-CSF)), various interferons (for example, IFN-γ, and the like), and other cytokines having effects on stem cells, for example, stem cell factor (SCF), and erythropoietin (Epo).

As used herein, "ROCK inhibitors" means substances that inhibit Rho kinase (ROCK: Rho-associated, coiled-coil containing protein kinase) and may be substances that inhibit either of ROCK I and ROCK II. The ROCK inhibitors are not particularly limited as long as they have the aforementioned function and examples include N-(4-pyridinyl)-4β-[(R)-1-aminoethyl]cyclohexane-1a-carboxamide (that may be also referred to as Y-27632), Fasudil (HA1077), (2S)-2-methyl-1-[(4-methyl-5-isoquinolinyl]sulfonyl]hexahydro-1H-1,4-diazepine (H-1152), 4β-[(1R)-1-aminoethyl]-N-(4-pyridyl)benzene-1zencarboxamide (Wf-536), N-(1H-pyrrolo[2,3-b]pyridin-4-yl)-4PER(R)-1-aminoethyl]cyclohexane-1α-carboxamide (Y-30141), N-(3-{[2-(4-amino-1,2,5-oxadiazol-3-yl)-1-ethyl-1H-imidazo[4,5-c]pyridin-6-yl]oxy}phenyl)-4-{[2-(4-morpholinyl)ethyl]oxy}benzamide (GSK269962A), N-(6-fluoro-1H-indazol-5-yl)-6-methyl-2-oxo-4-[4-(trifluoromethyl)phenyl]-3,4-dihydro-1H-pyridine-5-carboxamide (GSK429286A). The ROCK inhibitors are not limited to these and antisense oligonucleotides and siRNA to ROCK mRNA, antibodies that bind to ROCK, and dominant negative ROCK mutants can also be used as ROCK inhibitors, and commercially available, or synthesized according to a known method.

As used herein, "GSK3β inhibitors" are substances having the inhibitory activity for GSK3β (glycogen synthase kinase 3β). GSK3 (glycogen synthase kinase 3) is a serine/threonine protein kinase and involved in many signaling pathways associated with the production of glycogen, apoptosis, maintenance of stem cells, etc. GSK3 has the 2 isoforms α and β. "GSK3β inhibitors" used in the present invention are not particularly limited as long as they have the GSK3β-inhibiting activity and they may be substances having both the GSK3α-inhibiting activity and the GSK3β-inhibiting activity.

Examples of GSK3β inhibitors include CHIR98014 (2-[[2-[(5-nitro-6-aminopyridin-2-yl)amino]ethyl]amino]-4-(2,4-dichlorophenyl)-5-(1H-imidazol-1-yl)pyrimidine), CHIR99021 (6-[[2-[[4-(2,4-dichlorophenyl)-5-(4-methyl-1H-imidazol-2-yl)-2-pyrimidinyl]amino]ethyl]amino]nicotinonitrile), TDZD-8 (4-benzyl-2-methyl-1,2,4-thiadiazolidine-3,5-dione), SB216763 (3-(2,4-dichlorophenyl)-4-(1-methyl-1H-indol-3-yl)-1H-pyrrole-2,5-dione), TWS-119 (3-[6-(3-aminophenyl)-7H-pyrrolo[2,3-d]pyrimidin-4-yloxy]phenol), kenpaullone, 1-azakenpaullone, SB216763 (3-(2,4-dichlorophenyl)-4-(1-methyl-1H-indol-3-yl)-1H-pyrrole-2,5-dione), SB415286 (3-[(3-chloro-4-hydroxyphenyl)amino]-4-(2-nitrophenyl)-1H-pyrrole-2,5-dione), and AR-A0144-18, CT99021, CT20026, BIO, BIO-acetoxime, pyridocarbazole-ruthenium cyclopentadienyl complex, OTDZT, alpha-4-dibromoacetophenone, lithium, and the like. GSK3β is not limited to these and antisense oligonucleotides and siRNA to GSK3β mRNA, antibodies that bind to GSK313, dominant negative GSK3β mutants, and the like can also be used as GSK3β inhibitors, and commercially available, or synthesized according to a known method.

As used herein, examples of "serum replacement" include Knockout Serum Replacement (KSR: Invitrogen), StemSure Serum Replacement (Wako), B-27 supplement, N2-supplement, albumin (for example, lipid rich albumin), insulin, transferrin, fatty acids, collagen precursors, trace elements (for example, zinc, selenium (for example, sodium selenite)), 2-mercaptoethanol, 3'-thiolglycerol, or mixtures thereof (for example, ITS-G). Preferred serum replacements are B-27 supplement, KSR, StemSure Serum Replacement, ITS-G. The concentration of serum replacement in a medium when added into a medium is 0.01-10% by weight, and preferably 0.1-2% by weight. In the present invention, "serum replacement" is preferably used instead of serum.

As used herein, "FGFR1 inhibitor" is a substance having inhibitory activity for fibroblast growth factor receptor (FGFR) 1. FGFR1 is a member of the four-pass transmembrane tyrosine kinase family (FGFR1, FGFR2, FGFR3, and FGFR4), as a receptor having high affinity for growth factors FGF1 to FGF17. The FGFR1 inhibitor is not particularly limited as long as the FGFR1 inhibitor has FGFR1-inhibiting activity. The FGFR1 inhibitor may be a substance having the FGFR1-inhibiting activity as well as inhibitory activity for other FGFRs. In the present specification, "FGFR1 inhibitor" includes a substance having FGFR1-inhibiting activity, even if only slightly, and preferably refers to a substance that inhibits FGFR1 by 50% or more, more preferably a substance having a 50% inhibitory concentration ($IC_H$) of 1 μM or lower, further preferably 100 nM or lower, against FGFR1. A method for determining the FGFR1-inhibiting activity can be selected from known methods. Examples thereof include determination methods using EnzyChrom Kinase Assay Kit (BioAssay Systems). A conventionally known FGFR1 inhibitor may be used and can be found in patent literatures or non patent literatures.

More specifically, examples of the FGFR1 inhibitor that may be used in the present invention include PD-166866 (1-[2-amino-6-(3,5-dimethoxyphenyl)-pyrido(2,3-d)pyrimidin-7-yl]-3-tert-butylurea: (CAS No.: 192705-79-6), E-3810 (CAS No.: 1058137-23-7), PD-173074 (CAS No.: 219580-11-7), FGFR4-IN-1 (CAS No.: 1708971-72-5), FGFR-IN-1 (CAS No.: 1448169-71-8), FIIN-2 (CAS No.: 1633044-56-0), AZD4547 (CAS No.: 1035270-39-3), FIIN-3 (CAS No.:

1637735-84-2), NVP-BGJ398 (CAS No.: 1310746-10-1), NVP-BGJ398 (CAS No.: 872511-34-7), CH5183284 (CAS No.: 1265229-25-1), Derazantinib (CAS No.: 1234356-69-4), Derazantinib Racemate, Ferulic acid (CAS No.: 1135-24-6), SSR128129E (CAS No.: 848318-25-2), SSR128129E free acid (CAS No.: 848463-13-8), Erdafitinib (CAS No.: 1346242-81-6), BLU9931 (CAS No.: 1538604-68-0), PRN1371 (CAS No.: 1802929-43-6), 549076 (CAS No.: 1265965-22-7), LY2874455 (CAS No.: 1254473-64-7), Linsitinib (CAS No.: 867160-71-2), Dovitinib (CAS No.: 405169-16-6), Anlotinib (CAS No.: 1058156-90-3), Brivanib (CAS No.: 649735-46-6), Derazantinib (CAS No.: 1234356-69-4), Anlotinib Dihydrochloride (CAS No.: 1360460-82-7), ACTB-1003 (CAS No.: 939805-30-8), BLU-554 (CAS No.: 1707289-21-1), Rogaratinib (CAS No.: 1443530-05-9), BIBF 1120 esylate (CAS No.: 656247-18-6), TG 100572 Hydrochloride (CAS No.: 867331-64-4), ENMD-2076 (CAS No.: 934353-76-1), Brivanib alaninate (CAS No.: 649735-63-7), TG 100572 (CAS No.: 867334-05-2), BIBF 1120 (CAS No.: 656247-17-5), ENMD-2076 Tartrate (CAS No.: 1291074-87-7), TSU-68 (CAS No.: 252916-29-3), Ponatinib (CAS No.: 943319-70-8), Sulfatinib (CAS No.: 1308672-74-3), LY2784544 (CAS No.: 1229236-86-5), Dovitinib lactate (CAS No.: 692737-80-7), SU 5402 (CAS No.: 215543-92-3), FGF-401 (CAS No.: 1708971-55-4), Tyrosine kinase-IN-1 (CAS No.: 705946-27-6), PP58 (CAS No.: 212391-58-7), TG 100801 Hydrochloride (CAS No.: 1018069-81-2), Crenolanib (CAS No.: 670220-88-9), TG 100801 (CAS No.: 867331-82-6), Pazopanib Hydrochloride (CAS No.: 635702-64-6), Pazopanib (CAS No.: 444731-52-6), PD168393 (CAS No.: 194423-15-9), Apatinib (CAS No.: 1218779-75-9), Palbociclib isethionate (CAS No.: 827022-33-3), Foretinib (CAS No.: 849217-64-7), Lenvatinib (CAS No.: 417716-92-8), Tandutinib (CAS No.: 387867-13-2), and salts thereof (these compounds are referred to as compound group D). These compounds may each have one or more substituent(s) selected from those described above as long as the compound have FGFR1-inhibiting activity, preferably a 50% inhibitory concentration ($IC_{50}$) of 100 nM or lower against FGFR1.

The substructure (substituent, ring, etc.) of each of these compounds may be partially converted as long as the compound have FGFR1-inhibiting activity, preferably a 50% inhibitory concentration ($IC_{50}$) of 100 nM or lower against FGFR1.

In the present invention, the FGFR1 inhibitor is preferably CAS192705-79-6 (1-[2-amino-6-(3,5-dimethoxyphenyl)-pyrido(2,3-d)pyrimidin-7-yl]-3-tert-butylurea: CAS No.: 192705-79-6), E-3810 (CAS No.: 1058137-23-7), or PD173074 (CAS No.: 219580-11-7).

The FGFR1 inhibitor is not limited to the compounds described above, and an antisense oligonucleotide or siRNA against FGFR1 mRNA, an antibody binding to FGFR1, a dominant negative FGFR1 mutant, or the like can also be used as the FGFR1 inhibitor. Such an FGFR1 inhibitor is commercially available or can be synthesized according to a known method.

As used herein, "marker" means a cell antigen or a gene thereof that is specifically expressed depending on a predetermined cell type, such as "marker protein" and "marker gene". Preferably, a marker is a cell surface marker and this allows concentration, isolation, and/or detection of living cells. A marker can be a positive selection marker or a negative selection marker.

The detection of a marker protein can be conducted by an immunological assay, for example, ELISA, immunostaining, or flow cytometry using an antibody specific for the marker protein. The detection of a marker gene can be conducted by a method of amplifying and/or detecting nucleic acid known in the art, for example, RT-PCR, microarray, biochip, or the like. As used herein, "positive" for a marker protein means being detected to be positive by flow cytometry and "negative" therefor means being equal to or less than the lower detection limit in flow cytometry. Also, "positive" for a marker gene means being detected by RT-PCR and "negative" therefor means being equal to or less than the lower detection limit in RT-PCR.

As used herein, "expression" is defined as transcription and/or translation of a certain nucleotide sequence driven by an intracellular promoter.

As used herein, "cells" means a composition of cells, in other words, a cell population, unless otherwise specified. Accordingly, "cells" may include not only cells of specific type, but also cells of one or more other types. The proportion of cells of specific type in "cells" can be increased by enriching or purifying, or by depleting cells of one or more other types.

Herein, it is preferable that "cells" be human cells.

2. Composition Comprising Cells Derived from Pluripotent Stem Cells and Biocompatible Material

2-1. Cells Derived from Pluripotent Stem Cells

As used herein, "pluripotency" means the ability to differentiate into tissues and cells having various different shapes and functions and to differentiate into cells of any lineage of the 3 germ layers. "Pluripotency" is different from "totipotency", which is the ability to differentiate into any tissue of the living body, including the blastodisc, in that pluripotent cells cannot differentiate into the blastodisc and therefore, do not have the ability to form an individual.

As used herein, "multipotency" means the ability to differentiate into plural and limited numbers of linages of cells. For example, mesenchymal stem cells, hematopoietic stem cells, neural stem cells are multipotent, but not pluripotent.

As used herein, "pluripotent stem cells" refers to embryonic-stem cells (ES cells) and cells potentially having a pluripotency similar to that of ES cells, that is, the ability to differentiate into various tissues (all of the endodermal, mesodermal, and ectodermal tissues) in the living body. Examples of cells having a pluripotency similar to that of ES cells include "induced pluripotent stem cells" (that may be herein also referred to as "iPS cells"). In the present invention, preferably, pluripotent stem cells are human pluripotent stem cells.

Available "ES cells" include murine ES cells, such as various murine ES cell lines established by inGenious, RIKEN, and the like, and human ES cells, such as various human ES cell lines established by NIH, RIKEN, Kyoto University, Cellartis, and the like. For example, available ES cell lines include CHB-1 to CHB-12, RUES1, RUES2, HUES1 to HUES28, and the like from NIH; H1 and H9 from WisCell Research; and KhES-1, KhES-2, KhES-3, KhES-4, KhES-5, SSES1, SSES2, SSES3, and the like from RIKEN.

"Induced pluripotent stem cells" refers to cells obtained by reprograming mammalian somatic cells or undifferentiated stem cells by introducing particular factors (nuclear reprogramming factors). At present, there are various "induced pluripotent stem cells" and iPS cells established by Yamanaka, et al. by introducing the 4 factors Oct3/4, Sox2, Klf4, and c-Myc into murine fibroblasts (Takahashi K, Yamanaka S., Cell, (2006) 126: 663-676); iPS cells derived from human cells, established by introducing similar 4 factors into human fibroblasts (Takahashi K, Yamanaka S., et al. Cell, (2007) 131: 861-872.); Nanog-iPS cells established by cells using expression of Nanog as an indicator after introduction of the 4 factors (Okita, K., Ichisaka, T., and Yamanaka, S. (2007). Nature 448, 313-317.); iPS cells produced by a method not using c-Myc (Nakagawa M, Yamanaka S., et al. Nature Biotechnology, (2008) 26, 101-106); and iPS cells established by introducing 6 factors in a virus-free way (Okita K et al. Nat. Methods 2011 May; 8(5): 409-12, Okita K et al. Stem Cells. 31 (3) 458-66) may be also used. Also, induced pluripotent stem cells established by introducing the 4 factors OCT3/4, SOX2, NANOG, and LIN28 produced by Thomson et al. (Yu J., Thomson J A. et al., Science (2007) 318: 1917-1920.); induced pluripotent stem cells produced by Daley et al. (Park I H, Daley G Q. et al., Nature (2007) 451: 141-146); induced pluripotent stem cells produced by Sakurada et al. (Japanese Unexamined Patent Application Publication No. 2008-307007) and the like may be used.

In addition, any of induced pluripotent stem cells known in the art described in all published articles (for example, Shi Y., Ding S., et al., Cell Stem Cell, (2008) Vol 3, Issue 5, 568-574; Kim J B., Scholer H R., et al., Nature, (2008) 454, 646-650; Huangfu D., Melton, D A., et al., Nature Biotechnology, (2008) 26, No. 7, 795-797) or patents (for example, Japanese Unexamined Patent Application Publication No. 2008-307007, Japanese Unexamined Patent Application Publication No. 2008-283972, US2008-2336610, US2009-047263, WO2007-069666, WO2008-118220, WO2008-124133, WO2008-151058, WO2009-006930, WO2009-006997, WO2009-007852) may be used.

Available induced pluripotent cell lines include various iPS cell lines established by NIH, Institute of Physical and Chemical Research (RIKEN), Kyoto University and the like. For example, such human iPS cell lines include the RIKEN cell lines HiPS-RIKEN-1A, HIPS-RIKEN-2A, HiPS-RIKEN-12A, and Nips-B2 and the Kyoto University cell lines Ff-WJ-18, Ff-I01s01, Ff-I01s02, Ff-I01s04, Ff-I01s06, Ff-I14s03, Ff-I14s04, QHJI01s01, QHJI01s04, QHJI14s03, QHJI14s04, RWMH15s02, Ff-MH15s02, 253G1, 201B7, 409B2, 454E2, 606A1, 610B1, 648A1, CDI cell lines MyCell iPS Cells (21525.102.10A), MyCell iPS Cells (21526.101.10A), and the like.

As used herein, "cells derived from pluripotent stem cells" means cells obtained by induction of the differentiation of pluripotent stem cells, and examples of such cells include ectodermal cells, mesodermal cells, and endodermal cells differentiated from pluripotent stem cells, and cells consisting of any combination of those cells. More specifically, "cells derived from pluripotent stem cells" means cells differentiated from pluripotent stem cells and having functions comparable or similar to those of cells constituting an organ or tissue of, for example, the epidermis, nerves, brain, spinal cord, esophagus, stomach, small intestine, large intestine, bladder, urethra, lung, thyroid, pancreas, liver, muscles, skeleton, heart, blood vessels, spleen, or kidney (not limited to these), or precursor cells thereof.

In the present invention, "cells derived from pluripotent stem cells" preferably have a form of cell assemblies in each of which cells collect/aggregate together, that is, a form of spheroids. Spheroids of cells derived from pluripotent stem cells can be produced by a conventionally known approach such as suspension culture, or a culture plate for spheroid formation in which micro-spaces are disposed in the culture bottom surface (e.g., product name: Elplasia (Kuraray Co., Ltd.), product name: EZSPHERE (AGC TECHNO GLASS Co., Ltd.), product name: Corning spheroid microplate (Corning International K.K.)) may be used. Each spheroid has a size of about 10 µm to 1000 µm, preferably about 50 µm to 500 µm, more preferably about 50 µm to 300 µm, further preferably about 50 µm to 200 µm in diameter. And/or, each spheroid consists of about 100 to about 1000 cells, preferably about 200 to about 800 cells, more preferably about 300 to about 500 cells.

In one embodiment of the present invention, "cells derived from pluripotent stem cells" are definitive endoderm cells, primitive gut tube cells, posterior foregut cells, pancreatic progenitor cells, endocrine progenitor cells, or insulin-producing cells, which appear in the process of differentiation of pluripotent stem cells into pancreatic β cells, and particularly preferably insulin-producing cells.

It is known that cells having different features depending on the stages of differentiation appear in the process of differentiation of pluripotent stem cells into pancreatic β cells (WO2009/012428 and WO2016/021734). For example, the stages of differentiation can be broadly classified into pluripotent stem cells, definitive endoderm cells, primitive gut tube cells, posterior foregut cells, pancreatic progenitor cells, endocrine progenitor cells, insulin-producing cells, and pancreatic β cells in order from relatively undifferentiated to differentiated forms.

"Definitive endoderm cells" means cells characterized by expression of at least one marker of SOX17, FOXA2, BMP2, CER, and CXCR4.

"Primitive gut tube cells" means cells characterized by expression of at least one marker of HNF1B and HNF4A.

"Posterior foregut cells" means cells characterized by expression of at least one marker of PDX-1, HNF6, and HLXB9.

"Pancreatic progenitor cells" means cells characterized by expression of at least one marker of PDX-1, NKX6.1, PTF-1α, GATA4, and SOX9.

"Endocrine progenitor cells" means cells characterized by expression of at least one marker of chromogranin A, NeuroD, and Ngn3, and by no expression of any marker for the pancreas-associated hormone system (such as insulin). Endocrine progenitor cells may be expressing markers of PAX-4, NKX2-2, Islet-1, PDX-1, PTF-1α, etc.

"Insulin-producing cells" means cells characterized by expression of a marker of insulin. More specifically, "insulin-producing cells" is characterized by including cells expressing both markers of insulin and NKX6.1 (that is, insulin-positive and NKX6.1-positive cells, expressed as "Ins+NKX+ cells" hereinafter) at a proportion of about 30% or more, and including cells expressing only insulin of insulin and NKX6.1 (that is, insulin-positive and NKX6.1-negative cells, expressed as "Ins+NKX− cells" hereinafter) at a proportion of more than about 15%. The upper limit of the proportion of Ins+NKX+ cells in the insulin-producing cells is not particularly limited, and can be preferably about 50% or less.

The proportion of Ins+NKX− cells in the insulin-producing cells can be preferably about 20% or more, more preferably about 25% or more, further preferably about 30% or more. The upper limit of the proportion of Ins+NKX− cells in the insulin-producing cells is not particularly limited, and can be preferably about 40% or less.

For example, the insulin-producing cells comprise: Ins+NKX+ cells at a proportion of about 30% or more and about 50% or less; and Ins+NKX− cells at a proportion of more than about 15% and about 40% or less, preferably at a proportion of about 20% or more and about 40% or less, more preferably at a proportion of about 25% or more and about 40% or less, further preferably at a proportion of about 30% or more and about 40% or less.

Herein, the proportion of cells of specific type in the insulin-producing cells means the proportion to the total number of cells comprised in the insulin-producing cells. The proportion of cells of each type indicates a value in insulin-producing cells to be subjected to induction of differentiation into pancreatic islet-like cells (that is, subjected to transplantation into the living body).

Because more Ins+NKX− cells are found in immature insulin-producing cells (in an early stage of differentiation), a higher proportion of Ins+NKX− cells indicates that the insulin-producing cells are more immature insulin-producing cells (in an earlier stage of differentiation).

The insulin-producing cells can be further characterized by one or more selected from the following a to f:
 a. a low expression level of a MAFA gene or a protein thereof,
 b. a low proportion of Ki67-positive cells,
 c. a low proportion of glucagon-positive and insulin-negative cells,
 d. a characteristic to exhibit glucose-stimulated insulin secretion response,
 e. a high proportion of chromogranin A-positive cells, and
 f. a low proportion of alkaline phosphatase-positive pluripotent stem cells.
Here, "more" means 2, 3, 4, 5, or 6.

a. A Low Expression Level of a MAFA Gene or a Gene Product Thereof

The insulin-producing cells in the present invention are characterized in that the expression level of a MAFA gene or a protein encoded by the MAFA gene is lower than the expression level of a MAFA gene or a protein encoded by the MAFA gene in the pancreatic islet.

"Pancreatic islet" means cells in a more advanced stage of differentiation than insulin-producing cells, including mature pancreatic β cells and characterized by expression of at least one of MAFA, UCN3, and IAPP, which are markers of mature pancreatic β cells. A pancreatic islet isolated from a healthy individual can be used.

Comparison of expression levels of the MAFA gene or a protein encoded by the MAFA gene between insulin-producing cells and the pancreatic islet can be conducted using an approach known in the art, for example, in such a manner that the expression level of the MAFA gene or a protein encoded by the MAFA gene detected and quantified using an approach of, for example, RT-PCR, microarray, biochip, Western blotting, ELISA, immunostaining, or flow cytometry is corrected with the expression level of an internal standard gene or a protein encoded by the internal standard gene to obtain a relative value, which is used for comparison. "Internal standard gene" is not particularly limited, and GAPDH (glyceraldehyde-3-phosphate dehydrogenase), β-actin, β2-microglobuline, HPRT 1 (hypoxanthine phosphoribosyltransferase 1), etc., can be used.

The expression level of the MAFA gene or a protein encoded by the MAFA gene in the insulin-producing cells is about 20% or less, preferably about 15% or less, more preferably about 10% or less, further preferably about 5% or less, especially preferably about 1% or less of the expression level of the MAFA gene or a protein encoded by the MAFA gene in the pancreatic islet.

Because the MAFA gene or a protein encoded by MAFA gene is a marker of mature pancreatic β cells, the present feature indicates that the insulin-producing cells of the present invention are in such a stage of differentiation that the insulin-producing cells of the present invention comprise very few mature pancreatic β cells, or only a low proportion of mature pancreatic β cells.

b. A Low Proportion of Ki67-Positive Cells

The insulin-producing cells in the present invention are characterized by comprising Ki67-positive cells at a proportion of less than 3%.

"Ki67-positive cells" means highly proliferative cells coexisting in insulin-producing cells formed by induction of the differentiation of pluripotent stem cells and characterized by expression of Ki67 as a marker. "Ki67" is known as a cell cycle-related nucleoprotein and is also known as a marker of cell proliferation and cell cycle because its expression is found in the G1, S, G2, and M phases of proliferating cells and is not found in the G0 phase, a quiescent stage.

Hereinafter, "Ki67-positive" is also referred to as "Ki67+". "Ki67-positive cells" is also referred to as "Ki67+ cells".

The proportion of Ki67+ cells in the insulin-producing cells is about less than 3%, preferably about less than 1%, more preferably about less than 0.8%, further preferably about less than 0.5%.

The present feature indicates that the insulin-producing cells comprise very few coexisting or remaining Ki67+ cells, or comprise only a low proportion of coexisting or remaining Ki67+ cells. Ki67+ cells might adversely affect biological tissue-like structures finally obtained or influence the graft survival because of the high proliferative capacity, and coexisting or remaining Ki67+ cells are not preferred in some cases.

c. A Low Proportion of Glucagon-Positive and Insulin-Negative Cells

The insulin-producing cells in the present invention are characterized by comprising glucagon-positive and Ins− cells at a proportion of less than 3%. Hereinafter, "glucagon-positive" is also referred to as "Gcg+". "glucagon-positive and insulin-negative cells" are also referred to as "Gcg+Ins− cells".

The proportion of Gcg+Ins− cells in the insulin-producing cells is about 2.5% or less, preferably about 2% or less, more preferably about 1% or less, further preferably about 0.5% or less.

Because Gcg+Ins− is a marker of mature pancreatic α cells, the present feature indicates that the insulin-producing cells of the present invention are in such a stage of differentiation that the insulin-producing cells of the present invention comprise very few mature pancreatic α cells, or only a low proportion of mature pancreatic α cells.

d. A Characteristic to Exhibit Glucose-Stimulated Insulin Secretion Response

The insulin-producing cells in the present invention exhibit glucose-stimulated insulin secretion (GSIS) response.

The GSIS response by the insulin-producing cells can be evoked in accordance with a conventionally known approach (e.g., U.S. patent application Ser. No. 11/773,944), and can be evaluated, for example, by measuring the amount of C-peptide secreted into a medium. C-peptide is a decomposition product produced in an amount of moles equal to that of insulin during maturation of proinsulin. Measurement of the amount of C-peptide can be performed, for example, through ELISA using an anti-C-peptide monoclonal antibody.

e. A High Proportion of Chromogranin A-Positive Cells

The insulin-producing cells in the present invention are characterized by comprising chromogranin A-positive cells at a proportion of more than about 45%.

Hereinafter, "chromogranin A-positive" is also referred to as "Chga+". "Chromogranin A-positive cells" is also referred to as "Chga+ cells".

The proportion of Chga+ cells in the insulin-producing cells can be preferably about 50% or more (e.g., about 55% or more), more preferably about 60% or more, further preferably about 70% or more, furthermore preferably about 80% or more, especially preferably about 90% or more. The upper limit of the proportion of Chga+ cells in the insulin-producing cells is not particularly limited, and can be, for example, about 99% or less.

Chga+ cells include cells that secrete a hormone such as insulin (endocrine cells), and the above Ins+NKX+ cells and Ins+NKX− cells are also included in Chga+ cells. Accordingly, the present feature indicates that the insulin-producing cells of the present invention comprise endocrine cells at a high proportion.

f. A Low Proportion of Alkaline Phosphatase-Positive Pluripotent Stem Cells

The insulin-producing cells in the present invention are characterized by comprising alkaline phosphatase-positive pluripotent stem cells at a proportion of less than about 0.01%.

The proportion of alkaline phosphatase-positive pluripotent stem cells in the insulin-producing cells can be preferably about 0.008% or less, more preferably about 0.005% or less, further preferably about 0.001% or less.

Because alkaline phosphatase is a marker indicative of an undifferentiated state of pluripotent stem cells, the present feature indicates that the insulin-producing cells of the present invention comprise very few unintended pluripotent stem cells that have not undergone induction of differentiation, or comprise unintended pluripotent stem cells that have not undergone induction of differentiation at a low proportion.

Alkaline phosphatase-positive pluripotent stem cells may be further expressing an additional marker indicative of pluripotency. For the additional marker indicative of the pluripotency of pluripotent stem cells, at least one selected from NANOG, SOX2, SSEA-1, SSEA-3, SSEA-4, TRA-1-60, TRA-1-81, etc., can be used.

Induction of differentiation of pluripotent stem cells into definitive endoderm cells, primitive gut tube cells, posterior foregut cells, pancreatic progenitor cells, endocrine progenitor cells, and insulin-producing cells can be performed using the following steps of induction of differentiation:

step 1) inducing the differentiation of pluripotent stem cells into definitive endoderm cells;
step 2) inducing the differentiation of the definitive endoderm cells into primitive gut tube cells;
step 3) inducing the differentiation of the primitive gut tube cells into posterior foregut cells;
step 4) inducing the differentiation of the posterior foregut cells into pancreatic progenitor cells;
step 5) inducing the differentiation of the pancreatic progenitor cells into endocrine progenitor cells; and
step 6) inducing the differentiation of the endocrine progenitor cells into insulin-producing cells.

Hereinafter, each step will be described, though the induction of differentiation into each cell is not limited by these approaches.

Step 1) Differentiation into Definitive Endoderm Cells

The pluripotent stem cells are cultured in a medium containing a low dose of activin A to be allowed to differentiate into definitive endoderm cells.

The medium used in this step may be a basal medium for use in the culture of mammalian cells, such as RPMI medium, MEM medium, iMEM medium, DMEM (Dulbecco's Modified Eagle Medium) medium, Improved MEM Zinc Option medium, Improved MEM/1% B-27 supplement/Penicillin Streptomycin medium, or MCDB131/10 mM Glucose/20 mM Glucose/NaHCO$_3$/FAF-BSA/ITS-X/Glutamax/ascorbic acid/Penicillin Streptomycin medium.

Activin A can be contained in the medium at a low dose, for example, 5 to 10 ng/mL.

In another aspect, the concentration of activin A in the medium is about 0.1 to 100 ng/ml, preferably about 1 to 50 ng/ml, more preferably about 3 to 10 ng/ml.

The medium can be further supplemented with a ROCK inhibitor and a GSK3β inhibitor.

The concentration of the GSK3β inhibitor in the medium is appropriately set depending on the type of the GSK3β inhibitor used. For example, in the case of using CHIR99021 as the GSK3β inhibitor, its concentration is usually 2 to 5 μM, preferably 2 to 4 μM, particularly preferably about 3 μM.

The concentration of the ROCK inhibitor in the medium is appropriately set depending on the type of the ROCK inhibitor used. For example, in the case of using Y27632 as the ROCK inhibitor, its concentration is usually 5 to 20 μM, preferably 5 to 15 μM, particularly preferably about 10 μM.

The medium can be further supplemented with insulin. The insulin can be contained in an amount of 0.01 to 20 μM, preferably 0.1 to 10 μM, more preferably 0.5 to 5 μM, in the medium. The concentration of the insulin in the medium may be, but is not limited to, the concentration of insulin contained in added B-27 supplement.

The culture may be performed by any of two-dimensional culture and three-dimensional culture. For two-dimensional culture, the number of cells at the start of culture is not particularly limited and can be about 50000 to 1000000 cells/cm$^2$, preferably about 100000 to 800000 cells/cm$^2$, more preferably about 100000 to 300000 cells/cm$^2$. For three-dimensional culture, the number of cells at the start of culture is not particularly limited and can be about 10000 to 1000000 cells/mL, preferably about 100000 to 800000 cells/mL, more preferably about 300000 to 600000 cells/mL. The culture period is 1 day to 4 days, preferably 1 day to 3 days, particularly preferably 3 days.

The culture temperature is not particularly limited, and the culture is performed at 30 to 40° C. (for example, 37° C.). The concentration of carbon dioxide in a culture container is on the order of, for example, 5%.

Alternatively, in the present invention, the pluripotent stem cells can be subjected to first culture in a medium under conditions that allow the action of insulin in the presence of a low dose of activin A and subsequently subjected to second culture in a medium under conditions that do not allow the action of insulin for production of definitive endoderm cells.

(1) First Culture

"Conditions that allow the action of insulin" means conditions that cause the activation of the insulin signal transduction pathway in cells by insulin. In normal cases, insulin binds to the insulin receptor present on cell membrane surfaces to activate tyrosine kinase present within the receptor, thereby tyrosine-phosphorylating the insulin receptor substrate protein family (IRS: IRS-1, 2, 3). Herein, the occurrence of the series of reactions that is initiated by binding of insulin to the insulin receptor is expressed as "cause the activation of the insulin signal transduction pathway".

Examples of the conditions that allow the action of insulin include the case that insulin is contained in a medium. Insulin can be of any type that can activate the insulin signal transduction pathway in the pluripotent stem cells, and may be insulin produced using a recombinant method or insulin produced through synthesis using a solid-phase synthesis method. For example, insulin derived from a human, a nonhuman primate, a pig, cattle, a horse, sheep, a goat, a llama, a dog, a cat, a rabbit, a mouse, or a guinea pig can be used, and human insulin is preferred.

In the present invention, any insulin mutant, insulin derivative, or insulin agonist that can cause the activation of the insulin signal transduction pathway in the pluripotent stem cells can be used as "insulin". Examples of "insulin mutant" include: an insulin mutant possessing a polypeptide consisting of an amino acid sequence formed by deletion, substitution, addition, or insertion of 1 to 20 amino acids, preferably 1 to 10 amino acids, further preferably 1 to 5 amino acids, in the amino acid sequence of insulin and being capable of causing the activation of the insulin signal transduction pathway; and an insulin mutant possessing a polypeptide consisting of an amino acid sequence having a sequence identity of 80% or higher, more preferably 90% or higher, further preferably 95% or higher, the most preferably 99% or higher, to the amino acid sequence of insulin, and being capable of causing the activation of the insulin signal transduction pathway. Comparison of amino acid sequences can be performed using a known approach, and, for example, using BLAST (Basic Local Alignment Search Tool at the National Center for Biological Information), for example, with default settings. "Insulin derivative" means: a polypeptide consisting of an amino acid sequence formed by chemical substitution (e.g., α-methylation, α-hydroxylation), deletion (e.g., deamination), or modification (e.g., N-methylation) of some groups in the amino acid residues of insulin or an insulin mutant and being capable of causing the activation of the insulin signal transduction pathway; or a substance that exhibits the same action. "Insulin agonist" means a polypeptide capable of causing the activation of the insulin signal transduction pathway by binding to the insulin receptor irrespectively of the structure of insulin, or a substance that exhibits the same action.

Insulin can be contained in an amount of 0.01 to 20 µM, preferably 0.1 to 10 µM, more preferably 0.5 to 5 µM, in the medium for the first culture. The concentration of the insulin in the medium may be, but is not limited to, the concentration of insulin contained in added B-27 supplement.

The medium can be further supplemented with a ROCK inhibitor and/or a GSK3β inhibitor. The concentration of the ROCK inhibitor in the medium is appropriately set depending on the type of the ROCK inhibitor used. For example, in the case of using Y27632 as the ROCK inhibitor, its concentration is usually 5 to 20 µM, and can be preferably 5 to 15 µM, particularly preferably about 10 µM. The concentration of the GSK3β inhibitor in the medium is appropriately set depending on the type of the GSK3β inhibitor used. For example, in the case of using CHIR99021 as the GSK3β inhibitor, its concentration is usually 2 to 5 µM, and can be preferably 2 to 4 µM, particularly preferably about 3 µM.

The medium can be further supplemented with one or more selected from the group consisting of a pyruvate (e.g., a sodium salt), L-alanyl L-glutamine, and glucose. The medium can be supplemented with a pyruvate in an amount of 10 to 1000 mg/L, preferably 30 to 500 mg/L, more preferably 50 to 200 mg/L, particularly preferably about 110 mg/L. The medium can be supplemented with L-alanyl L-glutamine in an amount of 50 to 2000 mg/L, preferably 100 to 1500 mg/L, more preferably 500 to 1000 mg/L, particularly preferably about 860 mg/L. The medium can be supplemented with glucose in an amount of 15 mM or more, preferably 15 to 30 mM, more preferably 15 to 25, particularly preferably about 25 mM. The concentrations of the pyruvate, L-alanyl L-glutamine, and glucose in the medium may be, but are not limited to, the concentrations of the pyruvate, L-alanyl L-glutamine, and glucose contained in the DMEM medium (DMEM, high glucose, GlutaMAX™, pyruvate (Thermo Fisher Scientific)) or other DMEM medium.

A medium prepared with any of the above basal media as a base supplemented with one or more of the above components can be used for the medium. The basal medium is preferably DMEM medium, more preferably DMEM medium containing a pyruvate, L-alanyl L-glutamine, and glucose in the above amounts.

The culture period of the first culture can be in a range selected from 6 hours to 48 hours, preferably 12 to 24 hours. The culture temperature is not particularly limited, and the culture is performed at 30 to 40° C. (for example, 37° C.). The concentration of carbon dioxide in a culture container is on the order of, for example, 5%. The culture may be performed by any of two-dimensional culture and three-dimensional culture. For two-dimensional culture, the number of cells at the start of culture is not particularly limited and can be about 50000 to 1000000 cells/cm$^2$, preferably about 100000 to 800000 cells/cm$^2$, more preferably about 100000 to 300000 cells/cm$^2$. For three-dimensional culture, the number of cells at the start of culture is not particularly limited and can be about 10000 to 1000000 cells/mL, preferably about 100000 to 800000 cells/mL, more preferably about 300000 to 600000 cells/mL.

(2) Second Culture

"Conditions that do not allow the action of insulin" means conditions that do not cause the activation of the insulin signal transduction pathway in cells by insulin. "Do not cause the activation of the insulin signal transduction pathway" not only means causing completely no activation of the insulin signal transduction pathway, but also means causing only a slight activation of the insulin signal transduction pathway to such a degree that any significant difference as compared with the activation of the insulin signal transduction pathway in the absence of insulin is not found. Thus, examples of "conditions that do not allow the action of insulin" include the case that no insulin is contained in a medium, or, even if insulin is contained in a medium, the amount is such that only a slight activation is caused to such a degree that the significant difference is not found. Alternatively, "conditions that do not allow the action of insulin" means that even if insulin is contained in a medium, the activation of the insulin signal transduction pathway is not caused by virtue of inclusion of an insulin signal inhibitor together.

"Insulin signal inhibitor" means a component capable of blocking the insulin signal transduction pathway at any stage. Examples of the insulin signal inhibitor include polypeptides and compounds that bind to or compete with any of insulin, the insulin receptor, various proteins that act as a signaling substance, etc., to inhibit the intermolecular interaction in which such factors are involved. Examples of such an insulin signal inhibitor include LY294002 [2-(4-morpholinyl)-8-phenyl-4H-1-benzopyran-4-one], which competes with and inhibits binding of ATP to the catalytic subunit of PI3 kinase. The insulin signal inhibitor is not limited to these, and antibodies that bind to any of insulin, the insulin receptor, and various proteins that act as a signaling substance or dominant-negative mutants of the antibodies, and antisense oligonucleotides, siRNA, and the like for mRNA for any of the insulin receptor and various proteins that act as a signaling substance can also be used as the insulin signal inhibitor. The insulin signal inhibitor is commercially available or can be synthesized according to a known method.

The medium can be further supplemented with a ROCK inhibitor and/or a GSK3β inhibitor. The amount(s) of the ROCK inhibitor and/or GSK3β inhibitor in the medium can be selected from the ranges described above in the first culture, and may be the same as or different from the amount(s) for use in the first culture.

The medium can be further supplemented with one or more selected from the group consisting of a pyruvate, L-alanyl L-glutamine, and glucose. The amounts of the pyruvate, L-alanyl L-glutamine, and glucose in the medium can be selected from the ranges described above in the first culture, and may be the same as or different from the amounts for use in the first culture.

A medium prepared with a basal media for use in the culture of mammalian cells as a base supplemented with one or more of the above components can be used for the medium for use in the second culture. For the basal medium, the media described above in the first culture can be used, and the basal medium may be the same as or different from the basal medium for use in the first culture. The basal medium is preferably DMEM medium, more preferably DMEM medium containing a pyruvate, L-alanyl L-glutamine, and glucose in the above amounts.

The culture period of the second culture is at least 6 hours, and can be in a range selected preferably from 6 hours to 72 hours, further preferably from 24 to 72 hours. The culture temperature is not particularly limited, and the culture is performed at 30 to 40° C. (for example, 37° C.). The culture may be performed by any of two-dimensional culture and three-dimensional culture. The concentration of carbon dioxide in a culture container is on the order of, for example, 5%.

The media in the first culture and the second culture can be supplemented with the above low dose of activin A. The amount of activin A contained in the medium in the first culture and the amount of activin A contained in the medium in the second culture may be the same or different.

The media in the first culture and the second culture may be further supplemented with dimethyl sulfoxide.

The proportion of endocrine cells obtained after step 6) can be increased by culturing the pluripotent stem cells in the presence of a low dose of activin A, or by subjecting the pluripotent stem cells to the first culture in a medium under conditions that allow the action of insulin in the presence of a low dose of activin A and subsequently to the second culture in a medium under conditions that do not allow the action of insulin.

Step 2) Differentiation into Primitive Gut Tube Cells

The definitive endoderm cells obtained in step 1) are further cultured in a medium containing a growth factor to induce their differentiation into primitive gut tube cells. The culture period is 2 days to 8 days, preferably about 4 days.

The culture temperature is not particularly limited, and the culture is performed at 30 to 40° C. (for example, 37° C.). The concentration of carbon dioxide in a culture container is on the order of, for example, 5%. The culture may be performed by any of two-dimensional culture and three-dimensional culture.

Any of the basal media for use in the culture of mammalian cells described above in Step 1) can be used as culture medium. The medium may be appropriately supplemented with a serum replacement, a vitamin, an antibiotic, and the like, in addition to the growth factor.

The growth factor is preferably EGF, KGF, and/or FGF10, more preferably EGF and/or KGF, further preferably KGF.

The concentration of the growth factor in the medium is appropriately set depending on the type of the growth factor used and is usually about 0.1 nM to 1000 μM, preferably about 0.1 nM to 100 μM. In the case of EGF, its concentration is about 5 to 2000 ng/ml (that is, about 0.8 to 320 nM), preferably about 5 to 1000 ng/ml (that is, about 0.8 to 160 nM), more preferably about 10 to 1000 ng/ml (that is, about 1.6 to 160 nM). In the case of FGF10, its concentration is about 5 to 2000 ng/ml (that is, about 0.3 to 116 nM), preferably about 10 to 1000 ng/ml (that is, about 0.6 to 58 nM), more preferably about 10 to 1000 ng/ml (that is, about 0.6 to 58 nM). For example, in the case of using KGF as the growth factor, its concentration is usually 5 to 150 ng/mL, preferably 30 to 100 ng/mL, particularly preferably about 50 ng/mL.

Step 3) Differentiation into Posterior Foregut Cells

The primitive gut tube cells obtained in step 2) are further cultured in a medium containing a growth factor, cyclopamine, noggin, and the like to induce their differentiation into posterior foregut cells. The culture period is 1 day to 5 days, preferably about 2 days. The culture may be performed by any of two-dimensional culture and three-dimensional culture.

The culture temperature is not particularly limited, and the culture is performed at 30 to 40° C. (for example, 37° C.). The concentration of carbon dioxide in a culture container is on the order of, for example, 5%.

Any of the basal media for use in the culture of mammalian cells described above in Step 1) can be used as culture medium. The medium may be appropriately supplemented with a serum replacement, a vitamin, an antibiotic, and the like, in addition to the growth factor.

The growth factor is preferably EGF, KGF, and/or FGF10, more preferably EGF and/or KGF, further preferably KGF.

The concentration of the growth factor in the medium is appropriately set depending on the type of the growth factor used and is usually about 0.1 nM to 1000 μM, preferably about 0.1 nM to 100 μM. In the case of EGF, its concentration is about 5 to 2000 ng/ml (that is, about 0.8 to 320 nM), preferably about 5 to 1000 ng/ml (that is, about 0.8 to 160 nM), more preferably about 10 to 1000 ng/ml (that is, about 1.6 to 160 nM). In the case of FGF10, its concentration is about 5 to 2000 ng/ml (that is, about 0.3 to 116 nM), preferably about 10 to 1000 ng/ml (that is, about 0.6 to 58 nM), more preferably about 10 to 1000 ng/ml (that is, about 0.6 to 58 nM). For example, in the case of using KGF as the growth factor, its concentration is usually 5 to 150 ng/mL, preferably 30 to 100 ng/mL, particularly preferably about 50 ng/mL.

The concentration of the cyclopamine in the medium is not particularly limited and is usually 0.5 to 1.5 μM, preferably 0.3 to 1.0 μM, particularly preferably about 0.5 μM.

The concentration of the noggin in the medium is not particularly limited and is usually 10 to 200 ng/mL, preferably 50 to 150 ng/mL, particularly preferably about 100 ng/mL.

The medium may also be supplemented with dimethyl sulfoxide.

Step 4) Differentiation into Pancreatic Progenitor Cells

The posterior foregut cells obtained in step 3) may be further cultured in a medium containing a factor having CDK8/19-inhibiting activity, preferably a medium containing a factor having CDK8/19-inhibiting activity and a growth factor, to induce their differentiation into pancreatic progenitor cells. The culture period is 2 days to 10 days, preferably about 5 days. The culture may be performed by any of two-dimensional culture and three-dimensional culture. For two-dimensional culture, according to the previous report (Toyoda et al., Stem cell Research (2015) 14, 185-197), the posterior foregut cells obtained in step 3) are treated with 0.25% trypsin-EDTA and dispersed by pipetting and the dispersion is subjected to centrifugal separation to obtain cell suspension and then the suspension is reseeded to a fresh medium of step 4).

As in step 1), a basal medium for use in the culture of mammalian cells can be used as culture medium. The medium may be appropriately supplemented with a serum replacement, a vitamin, an antibiotic, and the like, in addition to the growth factor.

Each of the compounds mentioned above or salts thereof can be used as the factor having CDK8/19-inhibiting activity. The amount of the factor added to the medium is appropriately determined according to the compound or the salt thereof used and is usually about 0.00001 μM to 5 μM, preferably 0.00001 μM to 1 μM. The concentration of the factor having CDK8/19-inhibiting activity in the medium is preferably a concentration that attains inhibitory activity of 50% or more for CDK8/19.

The growth factor is preferably EGF, KGF, and/or FGF10, more preferably KGF and/or EGF, further preferably KGF and EGF.

The concentration of the growth factor in the medium is appropriately set depending on the type of the growth factor used and is usually about 0.1 nM to 1000 μM, preferably about 0.1 nM to 100 μM. In the case of EGF, its concentration is about 5 to 2000 ng/ml (that is, about 0.8 to 320 nM), preferably about 5 to 1000 ng/ml (that is, about 0.8 to 160 nM), more preferably about 10 to 1000 ng/ml (that is, about 1.6 to 160 nM). In the case of FGF10, its concentration is about 5 to 2000 ng/ml (that is, about 0.3 to 116 nM), preferably about 10 to 1000 ng/ml (that is, about 0.6 to 58 nM), more preferably about 10 to 1000 ng/ml (that is, about 0.6 to 58 nM). For example, in the case of using KGF and EGF as the growth factor, the concentration of EGF is usually 5 to 150 ng/mL, preferably 30 to 100 ng/mL, particularly preferably about 50 ng/mL, and the concentration of KGF is usually 10 to 200 ng/mL, preferably 50 to 150 ng/mL, particularly preferably about 100 ng/mL.

Culture on the first day in step 4) may be performed in the presence of a ROCK inhibitor, and culture on the following days may be performed in a medium containing no ROCK inhibitor.

The medium may also contain a PKC activator. PdBU (PKC activator II), TPB (PKC activator V), or the like is used as the PKC activator, though the PKC activator is not limited thereto. The concentration of the PKC activator to be added is about 0.1 to 100 ng/ml, preferably about 1 to 50 ng/ml, more preferably about 3 to 10 ng/ml.

The medium may also be supplemented with dimethyl sulfoxide or activin (1 to 50 ng/ml).

In any of the steps, the medium may be supplemented with a serum replacement (for example, B-27 supplement, ITS-G), in addition to the components described above. Also, an amino acid, L-glutamine, GlutaMAX (product name), a non-essential amino acid, a vitamin, nicotinamide, an antibiotic (for example, Antibiotic-Antimycotic (also referred to as AA herein), penicillin, streptomycin, or a mixture thereof), an antimicrobial agent (for example, amphotericin B), an antioxidant, pyruvic acid, a buffer, inorganic salts, and the like may be added thereto, if necessary. In the case of adding an antibiotic to the medium, its concentration in the medium is usually 0.01 to 20% by weight, preferably 0.1 to 10% by weight.

The culture may be performed by any of two-dimensional culture and three-dimensional culture. The culture temperature is not particularly limited, and the culture is performed at 30 to 40° C. (for example, 37° C.) The concentration of carbon dioxide in a culture container is on the order of, for example, 5%.

Step 5) Differentiation into Endocrine Progenitor Cells

The pancreatic progenitor cells obtained in step 4) are further cultured in a medium containing a growth factor to induce their differentiation into endocrine progenitor cells. The culture may be performed by any of two-dimensional culture and three-dimensional culture. For two-dimensional culture, the pancreatic progenitor cells obtained in step 4) are treated with 0.25% trypsin-EDTA and dispersed by pipetting and the dispersion is subjected to centrifugal separation to obtain cell suspension and then the suspension is reseeded to a fresh medium of step 5). The culture period is 2 days to 3 days, preferably about 2 days.

Any of the basal media for use in the culture of mammalian cells described above in Step 1) can be used as culture medium. The medium is supplemented with SANT1, retinoic acid, ALK5 inhibitor II, T3, and LDN according to the previous report (Nature Biotechnology 2014; 32: 1121-1133) and may be appropriately further supplemented with a Wnt inhibitor, a ROCK inhibitor, FGF (preferably FGF2), a serum replacement, a vitamin, an antibiotic, and the like. The medium may also be supplemented with dimethyl sulfoxide.

The culture is performed by nonadherent culture without the use of feeder cells. For the culture, a dish, a flask, a microplate, a porous plate (Nunc), or the like, or a bioreactor is used. The culture container is preferably surface-treated in order to decrease adhesiveness to cells.

The culture temperature is not particularly limited, and the culture is performed at 30 to 40° C. (for example, 37° C.). The concentration of carbon dioxide in a culture container is on the order of, for example, 5%.

Step 6) Differentiation into Insulin-Producing Cells

The endocrine progenitor cells obtained in step 5) are further cultured in a medium containing an FGFR1 inhibitor to induce their differentiation into insulin-producing cells. The culture period is 10 days to 30 days, preferably about 10 to 20 days.

Any of the basal media for use in the culture of mammalian cells described above in Step 1) can be used as culture medium. The medium is supplemented with ALK5 inhibitor II, T3, LDN, γ-secretase inhibitor XX, γ-secretase inhibitor RO, N-cysteine, an AXL inhibitor, and ascorbic acid according to the previous report (Nature Biotechnology 2014; 32: 1121-1133) and may be appropriately further supplemented with a Wnt inhibitor, a ROCK inhibitor, FGF (preferably FGF2), a serum replacement, a vitamin, an antibiotic, and the like. For example, the medium may be supplemented with ALK5 inhibitor II, T3, LDN, γ-secretase inhibitor RO, and ascorbic acid or may be supplemented with T3, ALK5 inhibitor II, $ZnSO_4$, heparin, N-acetylcysteine, Trolox, and R428.

The culture may be performed by any of two-dimensional culture and three-dimensional culture. The culture is performed by nonadherent culture without the use of feeder cells. For the culture, a dish, a flask, a microplate, a porous plate (Nunc), or the like, or a bioreactor is used. The culture container is preferably surface-treated in order to decrease adhesiveness to cells.

The culture temperature is not particularly limited, and the culture is performed at 30 to 40° C. (for example, 37° C.). The concentration of carbon dioxide in a culture container is on the order of, for example, 5%.

The FGFR1 inhibitor can be contained in any amount capable of inhibiting FGFR1 activity in the medium, and can be contained in an amount of, for example, 10 μM or less or 5 μM or less, preferably in an amount of less than 5 μM, less than 4 μM, less than 3 μM, or less than 2 μM. The lower limit of the amount of the FGFR1 inhibitor to be added is not particularly limited and can be 0.1 μM or more, preferably 0.5 μM or more. The amount of the FGFR1 inhibitor to be added is preferably less than 5 μM and 0.1 μM or more, more preferably less than 5 μM and 0.5 μM or more. The culture in the presence of the FGFR1 inhibitor can be performed for at least 12 hours, preferably 24 hours or longer, 2 days or longer, 4 days or longer, 8 days or longer, 10 days or longer, or 15 days or longer. The culture in the presence of the FGFR1 inhibitor is preferably performed for 4 days or longer. The culture in the presence of the FGFR1 inhibitor can be performed, for example, for about last 4 to 15 days, preferably about last 4 to 7 days, of step 6). The medium may be replaced during the period of treatment with the FGFR1 inhibitor and can be replaced with a medium supplemented with the FGFR1 inhibitor, having the same or different composition as or from that before the replacement, according to the culture schedule.

Culturing cells in a medium containing the FGFR1 inhibitor can inhibit the proliferation of Ki67-positive cells in the insulin-producing cells to be obtained.

The insulin-producing cells obtained in step 6) can be dissociated with an enzyme such as trypsin and collected. The insulin-producing cells collected can be cryopreserved until use. Then, the insulin-producing cells collected are seeded in the above medium in a number of about 500000 to 5000000 cells, preferably about 1000000 to 4000000 cells, more preferably about 2000000 to 3000000 cells per culture vessel or well and subjected to three-dimensional culture, and thereby insulin-producing cells can be obtained in a form of spheroids. Each spheroid consists of about 100 to about 1000 cells, preferably about 200 to about 800 cells, more preferably about 300 to about 500 cells.

2-2. Biocompatible Material

As used herein, "biocompatible material" means any material that does not induce significant immune response or adverse biological reaction (e.g., toxic reaction, coagulation) after transplanting in a living body followed by indwelling for a short or long period of time. Preferably, "biocompatible material" promotes angiogenesis and connective tissue production in a host after transplantion. In addition, it is preferable that "biocompatible material" be a biodegradable material. Examples of such materials include polylactic acid (PLA), polycaprolactone (PCL), polyurethane (PU), polyethylene glycol (PEG), polyhydroxyethyl methacrylate, polyglycolic acid (PGA), poly(lactic acid-co-glycolic acid) (PLGA), poly(3-hydroxybutyrate-co-hydroxyvalerate) (PHBV), poly(ethylene-co-vinyl acetate) (PEVA) polyacrylamide, polyethylene oxide, polyethyleneamine, polyhydroxybutyrate, poly(N-vinylpyrrolidone), polyvinyl alcohol, polypropylene fumarate, polyacrylic acid, poly(ε-caprolactone), polymethacrylic acid, polyvinylidene difluoride (PVDF), pectic acid, hyaluronic acid, heparin sulfate, chondroitin sulfate, heparan sulfate proteoglycan, heparin, chitin, chitosan, xanthan, carboxymethylcellulose, carboxymethylchitosan, alginic acid, alginate, collagen, cellulose, silk fibroin, keratin, gelatin, fibrin, pullulan, laminin, gellan, silicone, urethane, elastin, modified products of them, and combinations of them. If necessary, the surface of "biocompatible material" may be subjected to surface modification that allows adhesion of cells (e.g., a coating with a substrate for cell adhesion (such as collagen, gelatin, poly-L-lysine, poly-D-lysine, laminin, fibronectin, Matrigel, vitronectin)) or modified with a functional group known to control the proliferation, differentiation, or functions of cells (e.g., an amino group, a carboxyl group, a hydroxy group, a methacrylic acid group, an acrylic acid group). "Biocompatible material" can have any form such as a block, beads, a pellet, a sphere, a sheet, and a gel, and can be solid or porous. The shape of "biocompatible material" is preferably three-dimensional shape, and, may be, for example, a sphere, a polyhedron such as a tetrahedron and a hexahedron, a cylinder, a prism, a cone, a truncated cone, a pyramid, a truncated pyramid, a torus, a disk, an ellipsoid, or a deformed shape of any of them, and may be any shape that allows cells to disperse in the biocompatible material. The size of "biocompatible material" may be any size that allows transplantation and indwelling in a living body, and, for example, the longest side (diameter for a circle) can be about 0.1 to 3.0 cm, preferably about 0.5 to 2.0 cm, and the thickness can be about 0.1 to 2.0 cm, preferably about 0.3 to 1.5 cm. The number of cells comprised in the biocompatible material is about 500000 to 5000000 cells, preferably about 1000000 to 3000000 cells.

In another aspect, for example, the size of "biocompatible material" can be such that the longest side (diameter for a circle) is about 1 to 30 cm, preferably about 1 to 15 cm, more preferably about 2 to 10 cm.

A plurality of "biocompatible materials" may be transplanted and allowed to indwell.

In the present invention, "biocompatible material" is preferably in a gel (hydrogel). Gelation of the biocompatible material can be performed by using a known approach according to the biocompatible material, and can be performed, for example, by adding a crosslinking agent (e.g., metal cations such as calcium ions, magnesium ions, strontium ions, and barium ions, or salt forms of them) to an aqueous solution of the biocompatible material, or by allowing fibrinogen and thrombin to act in water. In the present invention, "biocompatible material" is particularly preferably a fibrin gel. The gel can contain the biocompatible material in any amount of about 0.01 to 10% by weight in an appropriate solvent (e.g., water, physiological saline, a medium).

In the present invention, the cells derived from pluripotent stem cells are disposed to be dispersed in the biocompatible material. "Disposed to be dispersed" means that the cells derived from pluripotent stem cells are disposed in a widely distributed manner in the biocompatible material without being localized at certain sites. If the cells derived from pluripotent stem cells have a form of spheroids, for example, "disposed to be dispersed" means that any adjacent spheroids are present with the biocompatible material intervening therebetween. If the cells derived from pluripotent stem cells have a form of spheroids, for example, "disposed to be dispersed" means that any adjacent spheroids are disposed with an interval of about 1 μm or larger, preferably about 5 μm or larger.

In another aspect, if the cells derived from pluripotent stem cells have a form of spheroids, "disposed to be dispersed" means that a certain proportion or more (30% or more, 40% or more, 50% or more, 60% or more, 70% or more, 80% or more, 90% or more, 95% or more) of the spheroids in the biocompatible material are disposed without being in contact with each other, and preferably means that 95% or more of the spheroids in the biocompatible material are disposed without being in contact with each other.

In another aspect, if the cells derived from pluripotent stem cells have a form of spheroids, "disposed to be dispersed" means that a certain proportion or more (30% or more, 40% or more, 50% or more, 60% or more, 70% or more, 80% or more, 90% or more, 95% or more) of the spheroids in the biocompatible material are spheroids of 50 to 500 μm in diameter (indicating that large spheroids are not formed by coming into contact with each other), and preferably means that 95% or more of the spheroids in the biocompatible material are spheroids of 50 to 500 μm in diameter.

In another aspect, if the cells derived from pluripotent stem cells have a form of spheroids, "disposed to be dispersed" means that the spheroids are three-dimensionally disposed like pin dots in the biocompatible material. "Three-dimensionally disposed like pin dots" means not only that the spheroids are three-dimensionally present in a manner that each spheroid keeps an interval from spheroids therearound, but also that the spheroids are three-dimensionally present in a manner that each spheroid is in contact with any of spheroids therearound. The spheroids may have the same size or different sizes. Here, "disposed to be dispersed" does not mean that spheroids are disposed in the biocompatible material and then aggregate/fuse to form larger spheroids.

Although "disposed to be dispersed" can be achieved by any approach, it can be performed by sufficiently stirring and mixing a solution of the cells derived from pluripotent stem cells and seeding the solution on the biocompatible material, and/or by adjusting the concentration of the cells derived from pluripotent stem cells to be seeded on the biocompatible material, and/or by adding the cells derived from pluripotent stem cells to a solution of the biocompatible material and sufficiently stirring and mixing the solution. If the biocompatible material is in a gel, for example, the cells derived from pluripotent stem cells can be disposed to be dispersed in the biocompatible material in such a manner that the cells derived from pluripotent stem cells are mixed in a solution of the biocompatible material before being gelled so that the number of the cells derived from pluripotent stem cells falls within 1000000 to 6000000 cells, preferably 2000000 to 5000000 cells per 50 to 200 μL, and the solution is stirred and gelled before the cells precipitate.

In another aspect, if the biocompatible material is in a gel, for example, the cells derived from pluripotent stem cells can be disposed to be dispersed in the biocompatible material in such a manner that the cells derived from pluripotent stem cells are mixed in a solution of the biocompatible material before being gelled so that the number of the cells derived from pluripotent stem cells falls within $1\times10^7$ to $1\times10^{10}$ cells, preferably $3\times10^8$ to $1\times10^9$ cells per 15 to 50 mL, and the solution is stirred and gelled before the cells precipitate.

3. Biological Tissue-Like Structure

Herein, "biological tissue-like structure" means a structure having functions comparable or similar to those of a biological organ or tissue of, for example, the epidermis, nerves, brain, spinal cord, esophagus, stomach, small intestine, large intestine, bladder, urethra, lung, thyroid, pancreas, liver, muscles, skeleton, heart, blood vessels, spleen, or kidney (not limited to these). The biological tissue-like structure can be obtained by transplanting a composition in which the cells derived from pluripotent stem cells are disposed to be dispersed in the biocompatible material into a living body of an animal for indwelling, and inducing the differentiation of the cells derived from pluripotent stem cells.

"Animal" is preferably a mammal. Examples thereof include humans, nonhuman primates, pigs, cattle, horses, sheep, goats, llamas, dogs, cats, rabbits, mice, and guinea pigs. A human is preferred.

The transplantation is preferably performed to an in vivo region where the composition can be fixed at a given position, and can be performed, for example, subcutaneously, intraperitoneally, to the peritoneal mesothelium, to the greater omentum, to a fat tissue, to a muscle tissue, or beneath the capsule of each organ such as the pancreas or the kidney, in the animal.

After transplantation, the cells derived from pluripotent stem cells in the composition are induced to differentiate in the in vivo environment, differentiating and maturing, and, according to "cells derived from pluripotent stem cells" used, a structure having functions comparable or similar to those of an organ or tissue of, for example, the epidermis, nerves, brain, spinal cord, esophagus, stomach, small intestine, large intestine, bladder, urethra, lung, thyroid, pancreas, liver, muscles, skeleton, heart, blood vessels, spleen, or kidney (not limited to these) can be obtained.

The biological tissue-like structure obtained may then be retrieved or allowed to indwell in the living body as it is.

The biological tissue-like structure may comprise: a plurality of clusters consisting of differentiated cells obtained by inducing differentiation of the cells derived from pluripotent stem cells; a connective tissue derived from the host animal; and blood vessels derived from the host animal.

The differentiated cells obtained by inducing differentiation of the cells derived from pluripotent stem cells form a plurality of clusters and are present to be dispersed in the biological tissue-like structure. Each cluster has a size of about 10 μm to 1000 μm, preferably about 50 μm to 500 μm, more preferably about 50 μm to 300 μm in diameter. And/or, each cluster consists of about 100 to about 1000 cells, preferably about 200 to about 800 cells, more preferably about 300 to about 500 cells. About 50 to 2000 clusters, preferably about 100 to 500 clusters are present to be dispersed in the biological tissue-like structure, and this number may change depending on the number of the cells derived from pluripotent stem cells disposed to be dispersed in the biocompatible material. "Present to be dispersed" means that the clusters of differentiated cells are present in a widely distributed manner in the biological tissue-like structure without being localized at certain sites. In addition, "present to be dispersed" means that any adjacent clusters are present with the connective tissue derived from the host animal intervening therebetween.

"Connective tissue derived from host animal" means an extracellular matrix produced by cells derived from an animal with the composition transplanted thereinto, and examples thereof include elastin, fibrillin, type I-collagen, and type III-collagen. The connective tissue derived from the host animal is present in such a manner that the connective tissue derived from the host animal surrounds the plurality of clusters of differentiated cells, and fills the space among clusters in the biological tissue-like structure.

"Blood vessels derived from host animal" means blood vessels that are formed by cells derived from an animal with the composition transplanted thereinto and connect to blood vessels of the host animal in the outside of the biological tissue-like structure. The blood vessels derived from the host animal are intruding into the clusters in the biological tissue-like structure, and circulate blood into the clusters to perform supply of oxygen, nutrients, and the like and excretion of waste products.

As one embodiment of the present invention, in the case that definitive endoderm cells, primitive gut tube cells, posterior foregut cells, pancreatic progenitor cells, endocrine progenitor cells, or insulin-producing cells, which appear in the process of differentiation of pluripotent stem cells into pancreatic β cells, preferably insulin-producing cells are used as the cells derived from pluripotent stem cells, these cells are induced to differentiate and mature in the above-described composition transplanted in a living body, and a biological tissue-like structure comprising differentiated cells having functions comparable or similar to those of the pancreatic islet (hereinafter, expressed as "pancreatic islet-like cells") can be obtained.

In the thus-obtained biological tissue-like structure, pancreatic islet-like cells can be characterized by one or more selected from the following (a) to (g):
  (a) expressing at least one marker of MAFA, UCN3, and IAPP,
  (b) a high proportion of chromogranin A-positive cells (Chga+ cells),
  (c) a low proportion of Ki67-positive cells (Ki67+ cells),
  (d) a high proportion of glucagon-positive and insulin-negative cells (Gcg+Ins− cells),
  (e) a characteristic to exhibit insulin-secreting action in response to low blood sugar,
  (f) comprising no exocrine cell, and
  (g) a high proportion of insulin-positive and glucagon-negative cells (Ins+Gcg− cells).

Here, "more" means 2, 3, 4, 5, 6, or 7.

Evaluation can be conducted on the presence or absence of the features (a) to (g) 4 weeks, preferably 8 weeks after induction of the differentiation of the insulin-producing cells (i.e., after transplantation of the above-described composition into the living body). The proportion of cells of specific type in pancreatic islet-like cells means the proportion of the cell to the total number of cells of cell clusters derived from a graft.

(a) Expressing at Least One Marker of MAFA, UCN3, and IAPP

The pancreatic islet-like cells comprise pancreatic β cells. Pancreatic β cells express at least one marker of MAFA, UCN3, and IAPP, which are maturation markers of pancreatic β cells. Pancreatic β cells can also be characterized by a reaction to increase insulin secretion by glucose stimulation.

(b) A High Proportion of Chga+ Cells

The pancreatic islet-like cells are characterized by comprising Chga+ cells at a proportion of about 50% or more. The proportion of Chga+ cells in the pancreatic islet-like cells is preferably about 60% or more, more preferably about 70% or more, furthermore preferably about 90% or more, especially preferably about 95% or more (e.g., about 97% or more, about 98% or more).

Chga+ cells include cells that secrete a hormone such as insulin and glucagon (endocrine cells), and the present feature indicates that the pancreatic islet-like cells comprise endocrine cells at a high proportion.

(c) A Low Proportion of Ki67+ Cells

The pancreatic islet-like cells are characterized by comprising Ki67-positive cells at a proportion of less than about 3%. The proportion of Ki67-positive cells in the pancreatic islet-like cells is preferably less than about 1%, more preferably less than about 0.8%, further preferably less than about 0.5%.

The present feature indicates that the pancreatic islet-like cells comprise very few Ki67+ cells, coexistence or remains of which may be unpreferred, or comprise Ki67+ cells at a very low proportion.

(d) A High Proportion of Gcg+Ins− Cells

The pancreatic islet-like cells are characterized by comprising Gcg+Ins− cells at a proportion of about 10% or more. The proportion of Gcg+Ins− cells in the pancreatic islet-like cells is preferably about 15% or more, more preferably about 20% or more, furthermore preferably about 25% or more. The upper limit of the proportion of Gcg+Ins− cells in the pancreatic islet-like cells is not particularly limited, and can be, for example, about 50% or less, preferably about 45% or less, more preferably about 40% or less.

Because being a marker of mature pancreatic α cells, Gcg+Ins− indicates that the pancreatic islet-like cells comprise mature pancreatic α cells at a higher proportion than insulin-producing cells. This indicates that the pancreatic islet-like cells are in a more mature stage of differentiation than insulin-producing cells.

(e) A Characteristic to Exhibit Insulin-Secreting Action in Response to Low Blood Sugar The pancreatic islet-like cells are characterized by exhibiting insulin-secreting action in response to low blood sugar. "Insulin-secreting action in response to low blood sugar" means that the amount of secreted insulin increases within 1 hour, 2 hours, 3 hours, 4 hours, or 5 hours after the occurrence of low blood sugar. "Low blood sugar" means the case that the glucose concentration in blood or in a medium is about 70 mg/dL or less. Measurement of the amount of secreted insulin can be performed using any conventionally known approach, which is not particularly limited, and can be achieved by measuring the amount of C-peptide in blood or in a medium.

On the occurrence of low blood sugar in the living body, in normal cases, the elevation of the blood glucose level is promoted through secretion of glucagon or the like, and at the same time insulin is secreted as antagonism against glucagon, controlling the blood glucose level. Similarly, the pancreatic islet-like cells of the present invention enable control of blood glucose levels against low blood sugar, and exhibit an action of promoting the elevation of the blood glucose level in response to low blood sugar and at the same time secreting insulin as antagonism against the elevation of the blood glucose level.

(f) Comprising No Exocrine Cell

The pancreatic islet-like cells are characterized by comprising no exocrine cell. That is, an exocrine cell, which typically constitutes most part (about 95%) of the pancreatic islet in the living body of animals and secretes pancreatic fluid containing digestive enzymes including amylase and lipase, is not comprised in the pancreatic islet-like cells. The term "comprising no exocrine cell" may encompass not only the case that the pancreatic islet-like cells comprise completely no exocrine cell, but also the case that the pancreatic islet-like cells comprise exocrine cells at a low proportion of 5% or less, 4% or less, 3% or less, 2% or less, 1% or less, or 0.5% or less.

(g) A High Proportion of Ins+Gcg− Cells

The pancreatic islet-like cells are characterized by a high proportion of Ins+Gcg− cells. The proportion of Ins+Gcg− cells in the pancreatic islet-like cells is preferably about 20% or more, more preferably about 30% or more, furthermore preferably about 40% or more. The upper limit of the proportion of Ins+Gcg− cells in the pancreatic islet-like cells is not particularly limited, and can be, for example, about 80% or less, preferably about 70% or less, more preferably about 60% or less.

Because being a marker of mature pancreatic β cells, Ins+Gcg− indicates that the pancreatic islet-like cells comprise mature pancreatic β cells at a higher proportion than insulin-producing cells. This indicates that the pancreatic islet-like cells are in a more mature stage of differentiation than insulin-producing cells.

In the case that the biological tissue-like structure comprises pancreatic islet-like cells, the pancreatic islet-like cells may form a cluster in which insulin-positive cells are disposed in the inner side and glucagon-positive cells are disposed in the outer side.

6. Applications

The biological tissue-like structure obtained by the present approach has, according to "cells derived from pluripotent stem cells" used, functions comparable or similar to those of an organ or tissue of, for example, the epidermis, nerves, brain, spinal cord, esophagus, stomach, small intestine, large intestine, bladder, urethra, lung, thyroid, pancreas, liver, muscles, skeleton, heart, blood vessels, spleen, or kidney (not limited to these), and can be used for enhancing or retaining the functions of the organ or tissue, or for assisting or supplementing the functions of the organ or tissue lowered or lost because of a disease, disorder, or the like.

As one embodiment of the present invention, in the case that the biological tissue-like structure comprises the above-described pancreatic islet-like cells, the biological tissue-like structure can improve and/or retain the blood glucose level in a patient by the action of insulin and glucagon secreted by pancreatic islet-like cells, and thus can control the blood glucose level to normal levels.

Accordingly, the biological tissue-like structure can be used for treatment or prophylaxis of a disease, a disorder, or a symptom for which improvement and/or retention of blood glucose levels is needed. Examples of the disease, disorder, or symptom include, but are not limited to, diabetes mellitus (type I diabetes mellitus, type II diabetes mellitus), abnormal fasting and postprandial glucose levels, and hypoglycemia (e.g., hypoglycemia by administration of insulin in a patient with diabetes mellitus). "Treatment" means treatment, curing, prevention, amelioration or remission of a disease, a disorder, or a symptom, or reduction of the progression speed of a disease, a disorder, or a symptom. "Prophylaxis" means reduction of the possibility or risk of the onset of a disease, a disorder, or a symptom, or retardation of the onset of a disease, a disorder, or a symptom.

The patient is a mammal, (for example, a mouse, a rat, a hamster, a rabbit, a cat, a dog, cattle, sheep, a monkey, and a human), preferably a human.

Hereinafter, the present invention will be described with reference to Examples. However, the present invention is not limited by these Examples.

EXAMPLES

Example 1: Production and Transplantation of Insulin-Producing Cells and Evaluation of Functions and Form Thereof (STZ-Nod-scid Mice)

1. Method (1) Preparation of Insulin-Producing Cells

The induction of differentiation of the iPS cell line Ff-I14s04 into insulin-producing cells was carried out with a three-dimensional culture method using a bioreactor according to step 1) to 6) above or the previous report (Nature Biotechnology 2014; 32: 1121-1133).

Specifically, the iPS cells were subjected to first culture under conditions that allow the action of insulin in a medium (DMEM/1% B27/Penicillin Streptomycin/dimethyl sulfoxide) containing a differentiation-inducing factor (GSK3β inhibitor, ROCK inhibitor, and low dose of activin A), and subsequently to second culture under conditions that do not allow the action of insulin in a medium (DMEM/1% B27/Penicillin Streptomycin/dimethyl sulfoxide) containing a differentiation-inducing factor (low dose of activin A) to obtain definitive endoderm cells.

An endocrine progenitor cell population obtained by induction of the differentiation of the definitive endoderm cells was cultured in a medium (Improved MEM/1% B27/Penicillin Streptomycin) containing a differentiation-inducing factor (ALK5 inhibitor II, T3, LDN, γ-secretase inhibitor RO, ascorbic acid) and an FGF receptor 1 inhibitor (PD-166866) for 8 days. Further, culture was performed with a medium (MCDB/ITS-X/2% BSA/20 mM glucose/NaHCO$_3$/Glutamax/Penicillin Streptomycin) containing a partially different differentiation-inducing factor (ALK5 inhibitor II, T3, ZnSO$_4$, heparin, N-acetylcysteine, Trolox, R428, Y-27632) and an FGF receptor 1 inhibitor (PD-166866) for 4 days to obtain insulin-producing cells in a form of spheroids.

(2) Evaluation of Protein Expressions of Insulin-Producing Cells Before Transplantation Protein expressions (insulin, NKX6.1, chromogranin, Ki67) of the insulin-producing cells produced in (1) were measured by flow cytometry.

(3) Dispersion and Gelation of Insulin-Producing Cells in Fibrin Gel

Fibrinogen (Merck Millipore, 341576-100MG) for producing a fibrin gel was dissolved in advance in a minimal essential medium (MCDB) to reach 10 mg/mL, and stored at −80° C. until use. Thrombin (Sigma-Aldrich Co. LLC, 10602400001) was dissolved in PBS(−) to reach 50 U/mL, and stored at −80° C. until use. The fibrinogen solution and the thrombin solution were dissolved for use immediately before use.

The spheroids of the insulin-producing cells produced in (1) (each having a size of about 50 to 500 μm in diameter, including 3000000 cells in total) were collected in 1.5-mL tube and precipitated. After precipitation, the culture solution was removed as much as possible, to which 100 μL of the fibrinogen solution was added, and the resultant was sufficiently stirred. Subsequently, the thrombin solution in a ½ volume (50 μL) of the fibrinogen solution was added before an aggregate precipitated. For 5 minutes or longer after addition of the thrombin solution, the resultant was left to stand at room temperature for gelation.

(4) Transplantation of Insulin-Producing Cells into Living Body and Evaluation of Functions of Formation Process of Biological Tissue-Like Structure The fibrin gel in which the insulin-producing cells were dispersed, prepared in (3), was subcutaneously transplanted into immunodeficient NOD/SCID mice in which diabetes mellitus had been induced with streptozotocin (STZ) (iPIC group). After transplantation, concentrations of human C-peptide (an index of insulin derived from the insulin-producing cells) in blood and blood glucose levels were measured to evaluate graft survival and functions of the insulin-producing cells. As controls, individuals without transplantation (sham group) and non-diabetes mellitus NOD/SCID mice (control group) were set, and the indexes were measured and evaluated.

(5) Evaluation of Response of Biological Tissue-Like Structure Derived from Insulin-Producing Cells to Glucose Loading Six months after the fibrin gel in which the insulin-producing cells were dispersed was subcutaneously transplanted, glucose was orally administered forcedly to temporarily elevate blood glucose levels, and response of the insulin-producing cells thereafter was evaluated by measuring glucose concentrations in plasma and human C-peptide concentrations in blood.

(6) General Staining and Evaluation of Protein Expressions for Biological Tissue-Like Structure Derived from Insulin-Producing Cells The biological tissue-like structure derived from insulin-producing cells excised 6 months after transplantation was fixed with paraformaldehyde. From the fixed biological tissue-like structure, paraffin sections and frozen sections were prepared. HE staining and Masson trichrome staining were performed for the paraffin sections. Expressions of intended proteins (human nuclei (HuN), PDX1, insulin (INS), glucagon (GCG), mouse CD31 (mCD31), chromogranin A (CHGA), Ki67) were evaluated by immunohistological staining for the frozen sections.

2. Results (1) Evaluation of Protein Expressions of Insulin-Producing Cells Before Transplantation For the insulin-producing cells before transplantation, FIG. 1 shows results of flow cytometry measurement, and Table 1 shows proportions of insulin-positive/NKX6.1-positive cells, proportions of chromogranin A-positive cells, and proportions of Ki67-positive cells. Of the insulin-producing cells before transplantation, 95% or more were chromogranin A-positive endocrine cells, and the insulin-producing cells were a cell population in which 42.6% of them were insulin-positive/NKX6.1-positive cells, which were to mature into β cells after transplantation, and 30.3% of them were insulin-positive/NKX6.1-negative cells, which were to mature into α cells. The proportion of Ki67-positive cells, where Ki67 is a proliferation marker, was a very small value of 0.4%.

TABLE 1

|  | Step 6 day 12 |
| --- | --- |
| Proportion of insulin-positive/NKX6.1-positive cells | 42.6% |
| Proportion of chromogranin A-positive cells | 97.3% |
| Proportion of insulin-positive/NKX6.1-negative cells | 30.3% |
| Proportion of Ki67-positive cells | 0.4% |

Figure 2:
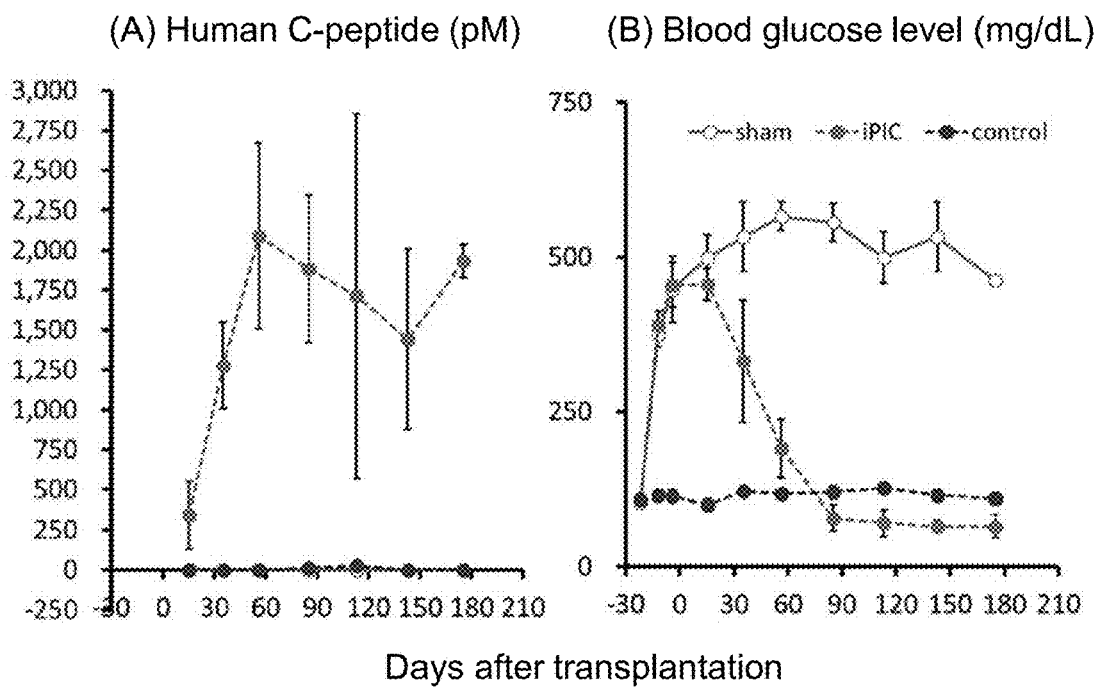
FIG. 2 shows results of measurement over time of human C-peptide concentrations in blood (A) and blood glucose levels (B) in immunodeficient NOD/SCID mice with a transplanted fibrin gel in which insulin-producing cells are dispersed, where diabetes mellitus has been induced with streptozotocin (STZ) in the mice.

(2) Evaluation of Functions of Process for Insulin-Producing Cells Transplanted into Living Body to Form Biological Tissue-Like Structure FIG. 2 and Table 2 show results of measurement of human C-peptide concentrations in blood and blood glucose levels after transplantation. For animals with the transplanted fibrin gel in which the insulin-producing cells were dispersed, high concentrations of human C-peptide were detected in blood 3 months after transplantation, and this was accompanied by improvement of high blood sugar. Blood glucose levels were retained at normal levels for 6 months. These suggested that the transplanted fibrin gel in which the insulin-producing cells are dispersed differentiates and mature in the subcutaneous site while being mixed with host cells to form a biological tissue-like structure that functions.

TABLE 2

| Group | Human C-peptide concentration in blood (pM) | | Blood glucose level (mg/dL) | | |
| --- | --- | --- | --- | --- | --- |
|  | 3 months after transplantation | After 6 months | At transplantation | After 3 months | After 6 months |
| sham | 0 ± 0 (N = 4) | 0, 0 (N = 2) | 448 ± 54 (N = 4) | 556 ± 30 (N = 4) | 483, 442 (N = 2) |
| iPIC | 1884 ± 463 (N = 5) | 1935 ± 104 (N = 3) | 455 ± 36 (N = 5) | 79 ± 21 (N = 5) | 65 ± 19 (N = 3) |
| control | 15 ± 26 (N = 3) | 0 ± 0 (N = 3) | 114 ± 10 (N = 4) | 119 ± 10 (N = 3) | 110 ± 4 (N = 3) |

Mean ± standard deviation for N = 3 or more, individual data for N = 2

Figure 3:
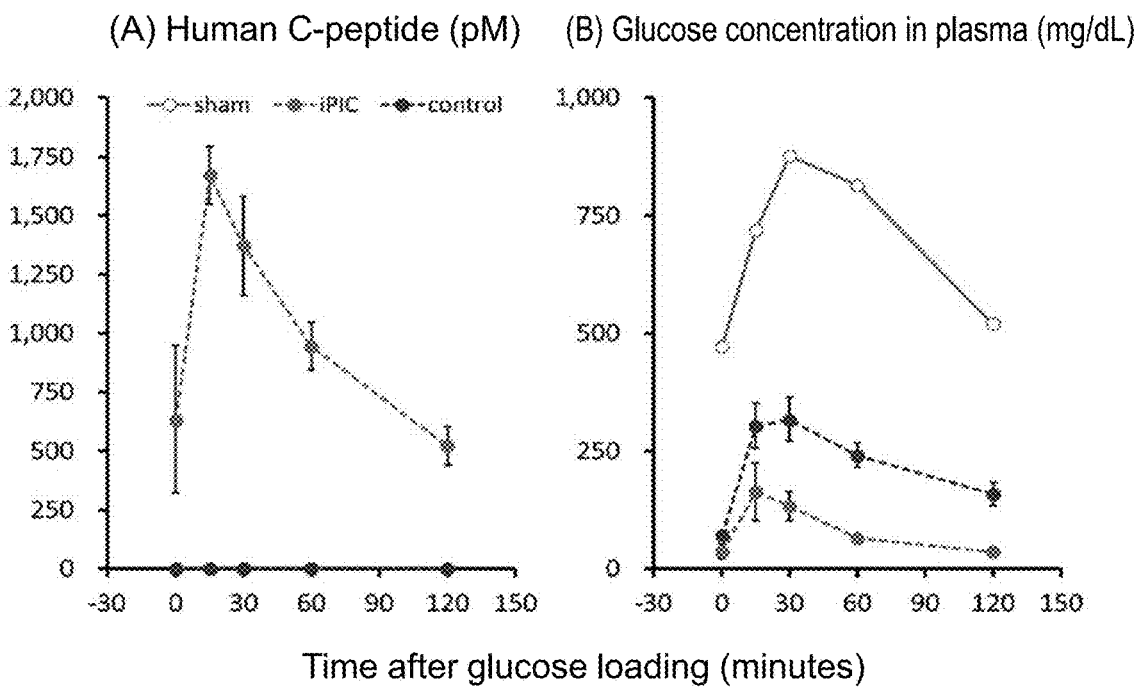
FIG. 3 shows analysis results for the response of a biological tissue-like structure derived from insulin-producing cells formed in the living bodies of immunodeficient NOD/SCID mice in which diabetes mellitus has been induced with streptozotocin (STZ) to glucose loading. Shown are results of measurement over time of human C-peptide concentrations in blood (A) and glucose concentrations in plasma (B) after glucose loading.

(3) Evaluation of Response of Biological Tissue-Like Structure Derived from Insulin-Producing Cells to Glucose Loading FIG. 3 shows human C-peptide concentrations in blood and glucose concentrations in plasma after glucose loading. The biological tissue-like structure formed by transplantation of the fibrin gel in which the insulin-producing cells were dispersed exhibited sharp glucose-responsive secretion of human C-peptide in blood 6 months after transplantation. In spite of the transplantation site, being a subcutaneous site, clear elevation of human C-peptide in blood was found 15 minutes after addition of glucose, and thus biological response mediated by abundant blood flow, closely resembling the actual pancreatic islet, was confirmed. In addition, reduced blood glucose was accompanied by reduction of human C-peptide in blood, and accordingly it is inferred that low blood sugar is less concerned.

Figure 4:
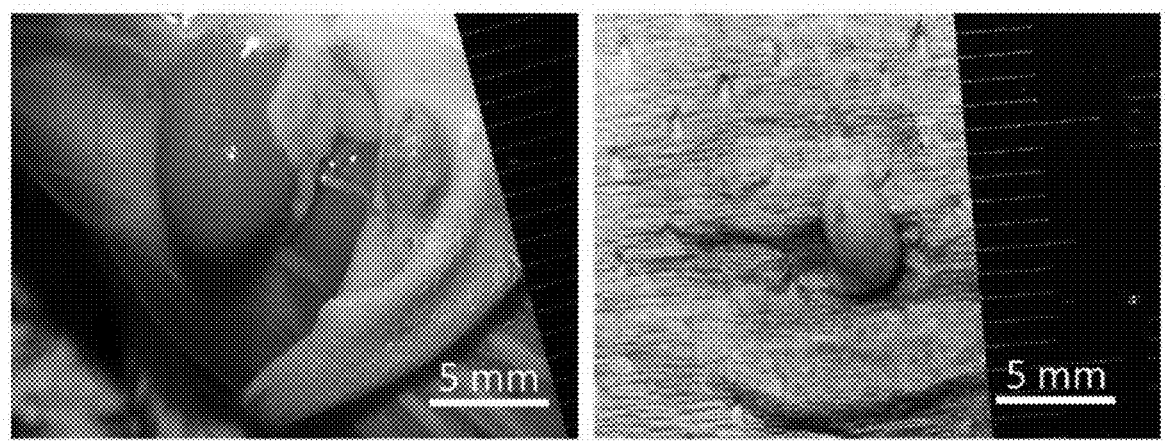
FIG. 4 shows photographs of a biological tissue-like structure derived from insulin-producing cells, the biological tissue-like structure excised from the interior of a living body 6 months after transplantation.
Figure 5:
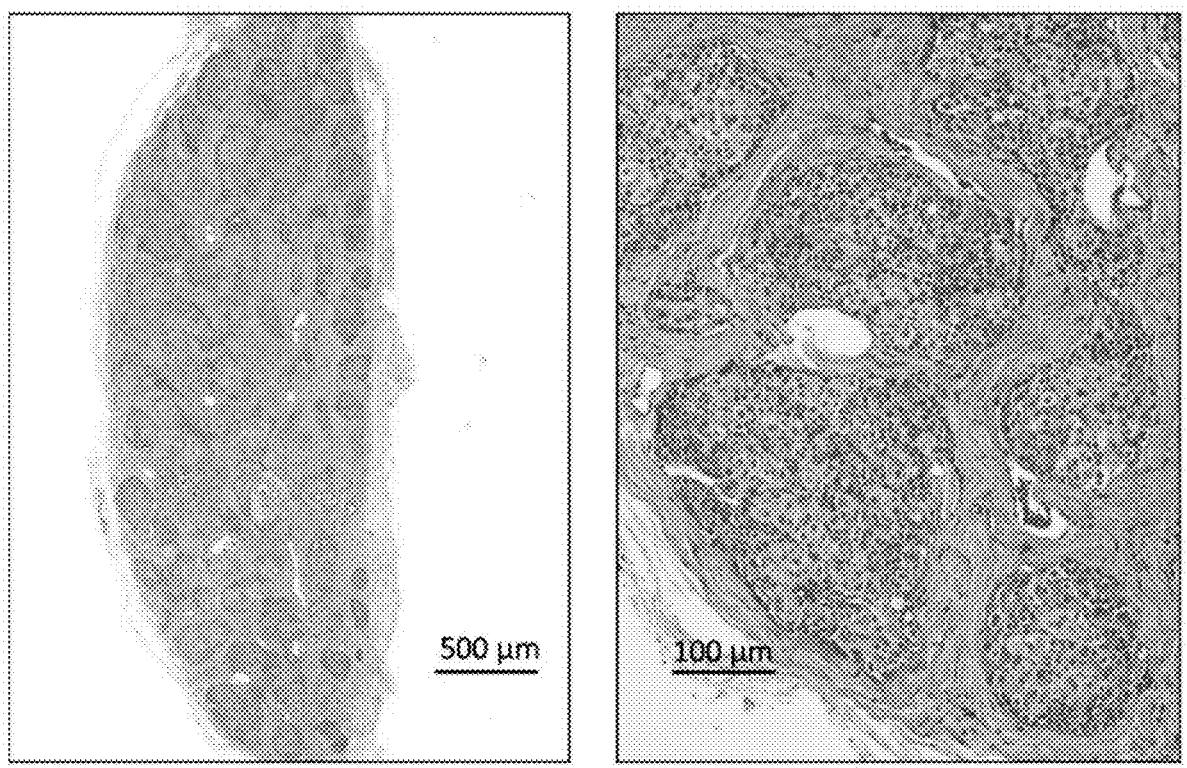
FIG. 5 shows HE-stained images of a biological tissue-like structure derived from insulin-producing cells, the biological tissue-like structure excised from the interior of a living body 6 months after transplantation.
Figure 6:
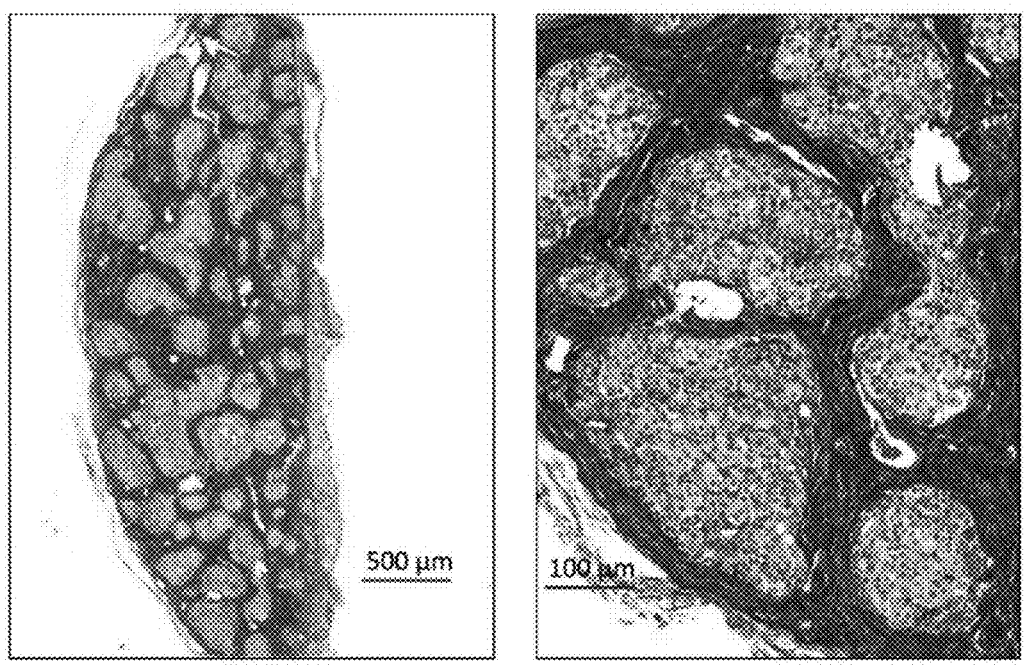
FIG. 6 shows Masson trichrome-stained images of a biological tissue-like structure derived from insulin-producing cells, the biological tissue-like structure excised from the interior of a living body 6 months after transplantation.
Figure 7:
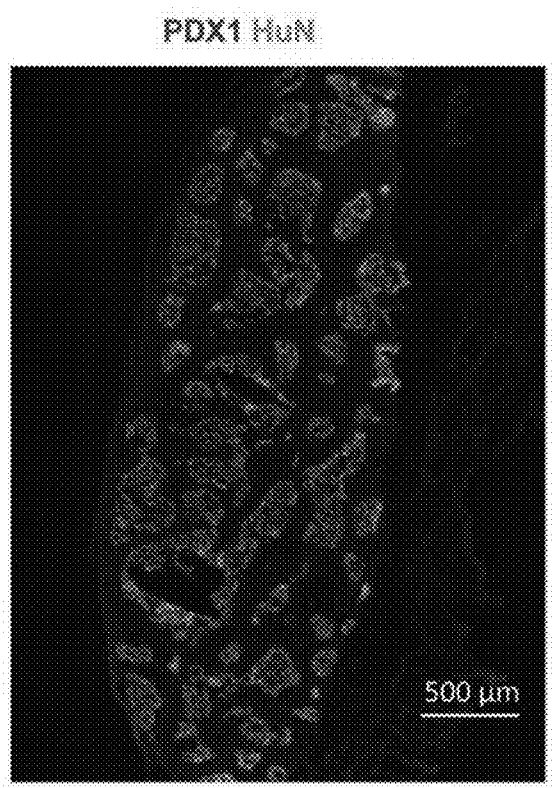
FIG. 7 shows an immunohistologically stained image of a biological tissue-like structure derived from insulin-producing cells for human nuclei (HuN) and PDX1, the biological tissue-like structure excised from the interior of a living body 6 months after transplantation.
Figure 8:
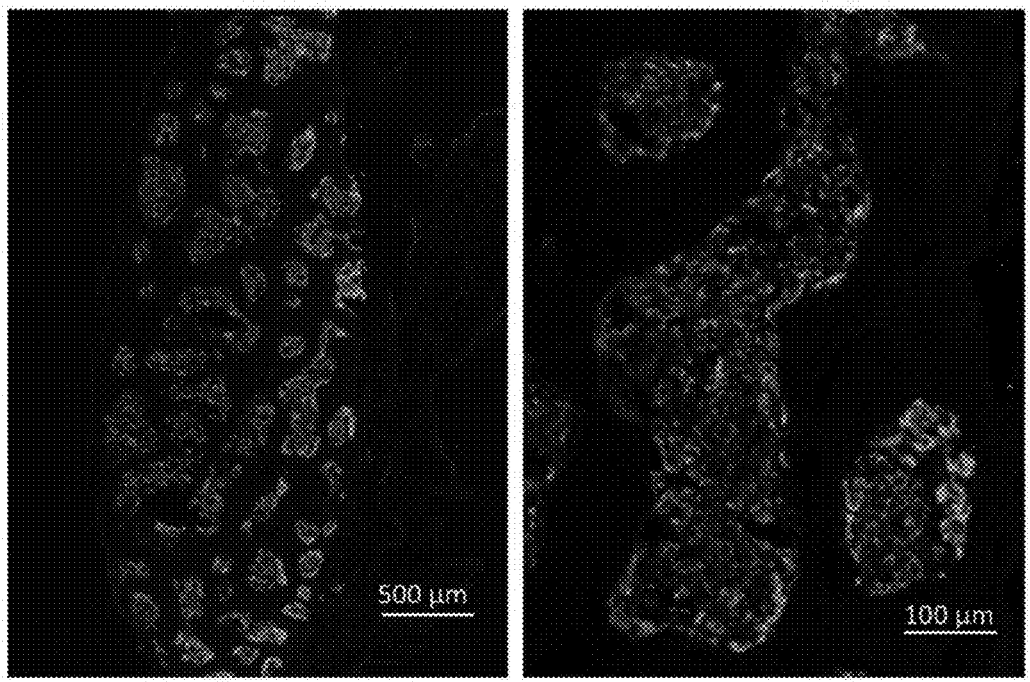
FIG. 8 shows immunohistologically stained images of a biological tissue-like structure derived from insulin-producing cells for insulin (INS) and glucagon (GCG), the biological tissue-like structure excised from the interior of a living body 6 months after transplantation.
Figure 9:
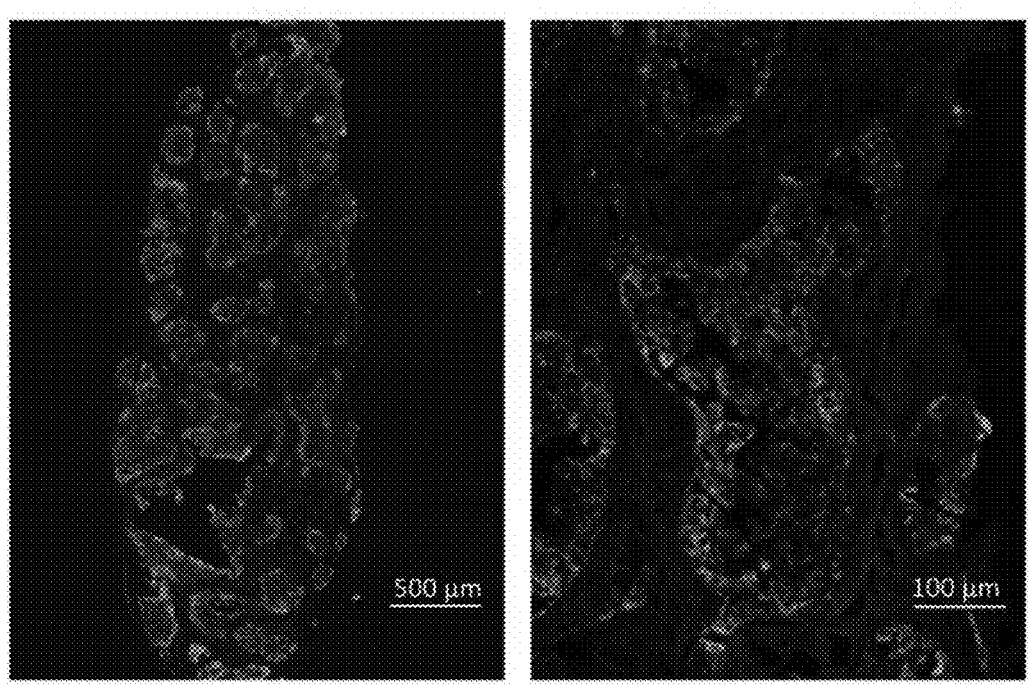
FIG. 9 shows immunohistologically stained images of a biological tissue-like structure derived from insulin-producing cells for mouse CD31 (mCD31) and chromogranin A (CHGA), the biological tissue-like structure excised from the interior of a living body 6 months after transplantation.

(4) Common Staining and Evaluation of Protein Expressions for Biological Tissue-Like Structure Derived from Insulin-Producing Cells FIG. 4 shows the gross appearance of the biological tissue-like structure derived from insulin-producing cells 6 months after transplantation, FIG. 5 shows HE-stained images of the excised biological tissue-like structure, FIG. 6 shows Masson trichrome-stained images thereof, and FIGS. 7 to 10 show results of immunohistological staining for expressions of intended proteins.

The gross appearance of the biological tissue-like structure derived from insulin-producing cells (FIG. 4) showed that the biological tissue-like structure was of rice grain size without noticeable swelling, and the biological tissue-like structure could be isolated from the subcutaneous site with ease. Dissection was conducted for four mice in total at the same period, and all the mice exhibited the mentioned gross appearance. Histological evaluation showed that the biological tissue-like structure was composed of 1) clusters of pancreatic islet-like cells derived from insulin-producing cells each having a diameter of 50 to 500 μm, 2) a host-derived fibrous tissue disposed to surround them, and 3) a host-derived vascular structure (FIGS. 5 to 10).

The host-derived vascular structure of 3) (=mouse CD31 positive, FIG. 9) was intruding primarily into clusters of endocrine cells of 1), and many erythrocytes were found in the clusters of pancreatic islet-like cells of 1) (FIGS. 5, 6). Accordingly, it is strongly suggested that the present biological tissue-like structure achieved abundant blood flow and sharp biological reaction mediated by the blood flow, like the actual pancreatic islet. In addition, the physical strength is high because of the richness in fibrous tissue (FIG. 6). When cleavage of the biological tissue-like structure derived from insulin-producing cells was actually attempted, the biological tissue-like structure derived from insulin-producing cells had cartilage-like strength and did not allow easy cleavage.

Figure 10:
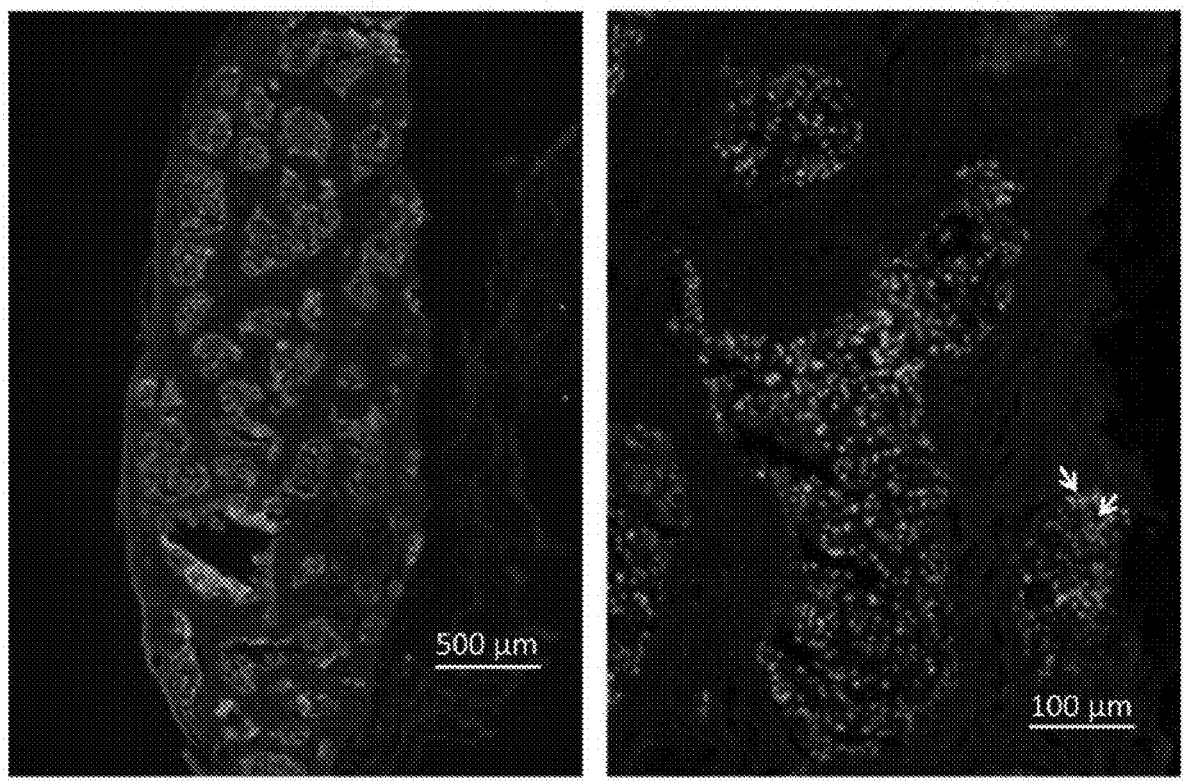
FIG. 10 shows immunohistologically stained images of a biological tissue-like structure derived from insulin-producing cells for human nuclei (HuN) and Ki67, the biological tissue-like structure excised from the interior of a living body 6 months after transplantation. Arrows: Ki67-positive cells.

Most of the HuN-positive cells derived from insulin-producing cells were pancreatic islet-like cells (FIGS. 7 to 10), and proliferation of unintended cells was not found. Further, Ki67-positive/HuN-positive cells, where Ki67 is a proliferation marker, were as few as 0.5% or less (FIG. 10). Insulin-positive cells were distributed in the inner side of each cluster of pancreatic islet-like cells of 1), and glucagon-positive cells were distributed in the outer side of each cluster of pancreatic islet-like cells of 1); such disposition is observed in the fetal human pancreas before birth or the rodent pancreatic islet. Therefore, it is suggested that the present biological tissue-like structure is capable of functioning for a period in the order of several decades like the fetal human pancreas islet.

From the above results, it was demonstrated that the insulin-producing cells, dispersed in a fibrin gel and transplanted into a living body, achieves long-term graft survival in a subcutaneous site, a site poor in blood flow and nutrients, and further mature while being mixed with cells of the host to form a new biological tissue-like structure. The subcutaneous biological tissue-like structure formed was demonstrated to have blood glucose level control function accompanied by physiological and sharp insulin secretion regulation, like the actual in vivo pancreatic islet.

Example 2: Formation of Biological Tissue-Like Structure Derived from Insulin-Producing Cells in Living Body with Pathological Condition of Diabetes Mellitus and Evaluation of Functions Thereof 1. Method The fibrin gel in which the insulin-producing cells were dispersed, prepared in (3) of Example 1 above, was subcutaneously transplanted into immunodeficient NOD/SCID mice in which diabetes mellitus had been induced with streptozotocin (STZ), or non-diabetes mellitus NOD/SCID mice. For 28 weeks after transplantation, postprandial human C-peptide and glucagon in blood, and blood glucose levels were measured.

For all the individuals after 28 weeks, the biological tissue-like structure derived from insulin-producing cells was excised. Each excised graft biological tissue-like structure was weighed, crushed, and subjected to acid-ethanol treatment, and thereafter, insulin and glucagon contents in the graft biological tissue-like structure were measured. As controls, the pancreas of each mouse with transplantation and the pancreas of each non-diabetes mellitus NOD/SCID mouse without transplantation were collected, and hormone contents were measured in the same manner.

2. Results

Figure 11:
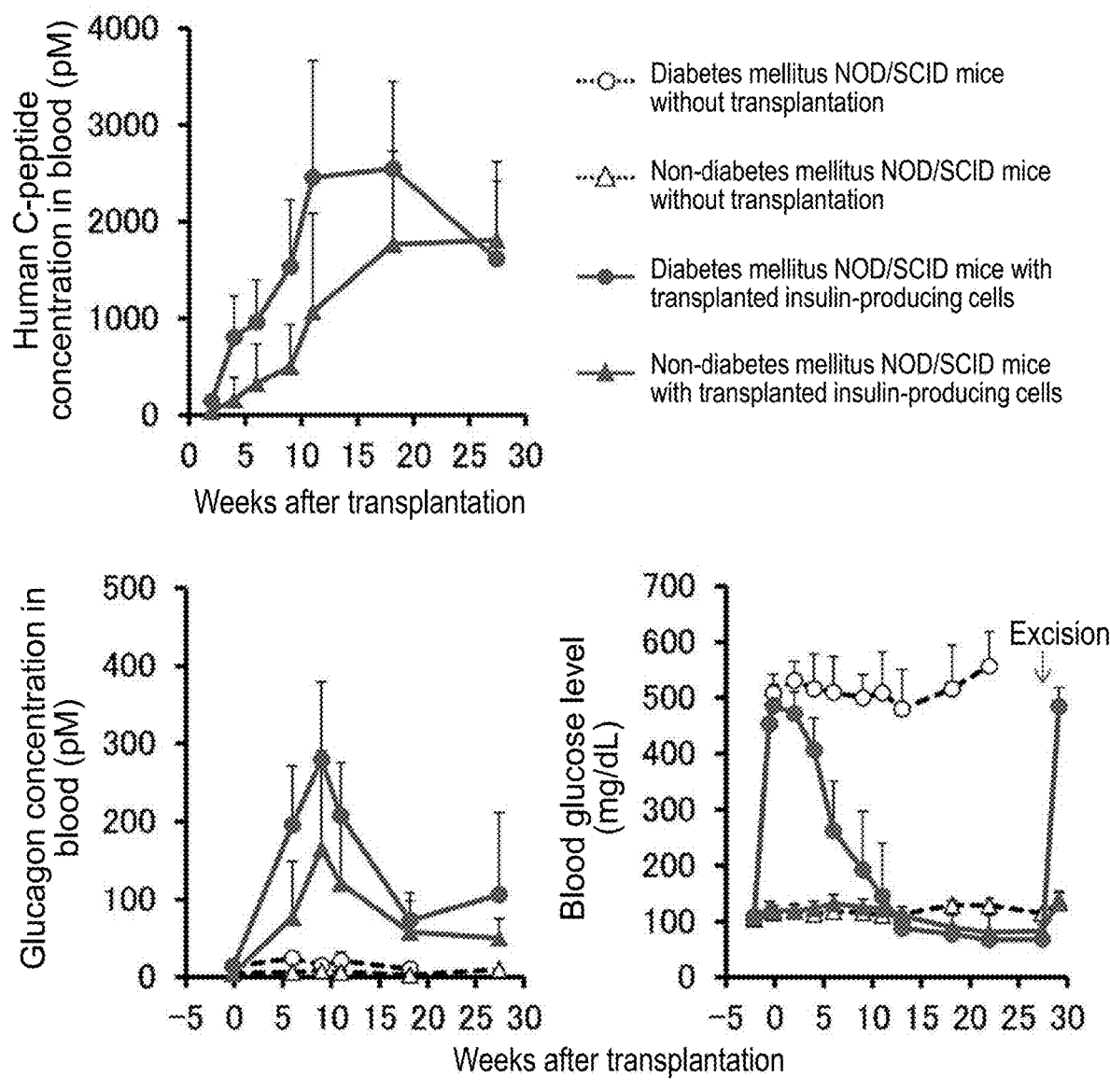
FIG. 11 shows measurement over time of human C-peptide and glucagon in blood, and blood glucose levels after transplanting insulin-producing cells dispersed in a fibrin gel into immunodeficient NOD/SCID mice in which diabetes mellitus has been induced with streptozotocin (STZ).

FIG. 11 shows transition of concentrations of human C-peptide and glucagon in blood and blood glucose levels. Human C-peptide was continuously detected in blood for 28 weeks after transplantation of the fibrin gel in which the insulin-producing cells were dispersed. The glucagon concentrations in blood also increased, being higher values than diabetes mellitus and non-diabetes mellitus mice without transplantation exhibited. It was suggested that the fibrin gel in which the insulin-producing cells were dispersed achieves long-term graft survival in a subcutaneous environment, and the biological tissue-like structure formed releases multiple pancreatic islet hormones. The high blood sugar in the diabetes mellitus mice was improved in 12 weeks after transplantation, and the blood glucose levels were retained in a normal range for 28 weeks. High blood sugar condition before transplantation completely came back when the biological tissue-like structure was excised, and hence it was demonstrated that the continuous, stable action to improve high blood sugar is derived from the biological tissue-like structure.

Figure 12:
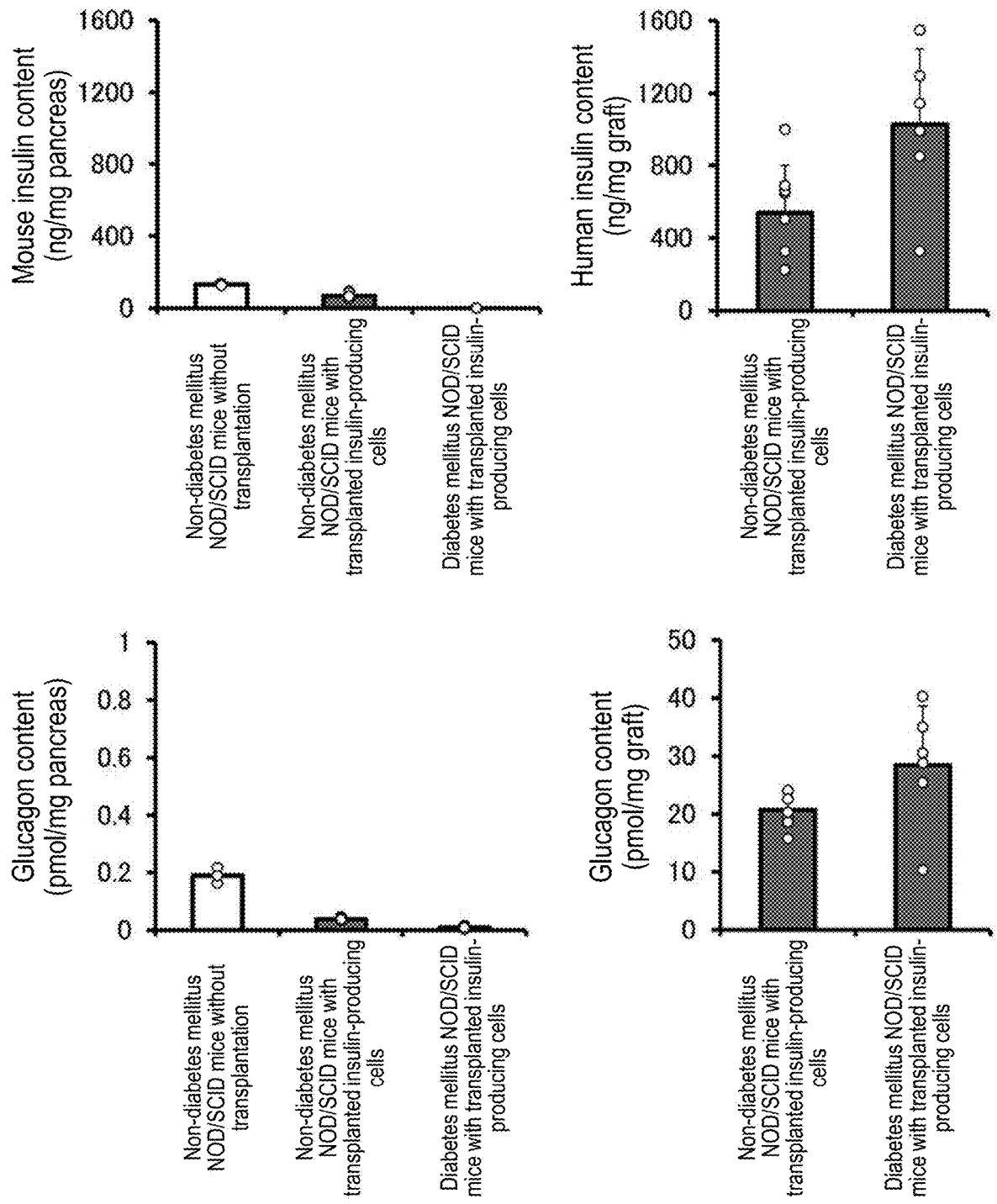
FIG. 12 shows results of measurement of insulin and glucagon contents in biological tissue-like structures derived from insulin-producing cells obtained by transplanting insulin-producing cells dispersed in a fibrin gel into immunodeficient NOD/SCID mice in which diabetes mellitus has been induced with streptozotocin (STZ) and non-diabetes mellitus NOD/SCID mice and excising from the interiors of their living bodies 28 weeks after transplantation. The top graphs show results of measurement of insulin contents, the bottom graphs show results of measurement of glucagon contents, the left graph in each of the top and bottom graphs shows results of measurement of hormone contents of interest in the pancreas of the mice (control), and the right graph in each of the top and bottom graphs shows results of measurement of hormone contents of interest in excised biological tissue-like structures derived from insulin-producing cells.

FIG. 12 shows hormone contents in the graft biological tissue-like structures and those in the pancreas. The insulin and glucagon contents per weight in the graft biological tissue-like structures (right) were higher than those in the pancreas (left). The graft biological tissue-like structures were demonstrated to contain pancreatic endocrine cells at a high density like the pancreatic islet in the pancreas.

Example 3: Blood Sugar Control Function of Biological Tissue-Like Structure Derived from Insulin-Producing Cells 1. Method The fibrin gel in which the insulin-producing cells were dispersed, prepared in (3) of Example 1 above, was subcutaneously transplanted into immunodeficient NOD/SCID mice in which diabetes mellitus had been induced with streptozotocin (STZ), or NOD/SCID mice having an Akita gene mutation, which causes spontaneous onset of diabetes mellitus. After lapse of 14 weeks after transplantation, the following tests were conducted with the use of mice whose high blood sugar completely improved.

Test (1): Glucose was orally administered forcedly to temporarily elevate blood glucose levels, and the subsequent response of the biological tissue-like structure derived from insulin-producing cells was evaluated by measuring human C-peptide, glucagon, and glucagon-like peptide-1 concentrations in blood. Non-diabetes mellitus NOD/SCID mice without transplantation were used as a control, and endogenous hormone concentrations in blood were measured.

Test (2): To evaluate the involvement of glucagon in the response of the biological tissue-like structure derived from insulin-producing cells, the glucagon receptor antagonist MK-0893 was orally administered forcedly before the forced administration of glucose, and a test was conducted in the same manner as test (1). MK-0893 exhibits stronger antagonistic activity to the human glucagon receptor than to the mouse glucagon receptor (J Med Chem. 2012 Jul. 12; 55 (13):6137-48).

Test (3): To evaluate the involvement of glucagon-like peptide-1 in the insulin release by the biological tissue-like structure derived from insulin-producing cells, the glucagon-like peptide-1 receptor antagonist Exendin-9 was subcutaneously administered continuously for 3 days with an osmotic pump, and human C-peptide concentrations in blood before and after administration were measured.

Test (4): The insulin formulation glargine was subcutaneously administered to induce low blood sugar, and the subsequent response of the biological tissue-like structure derived from insulin-producing cells was evaluated by measuring human C-peptide in blood. As a control, non-diabetes mellitus NOD/SCID mice without transplantation were used, and blood concentrations of endogenous pancreatic islet-derived mouse C-peptide were measured.

2. Results

Figure 13:
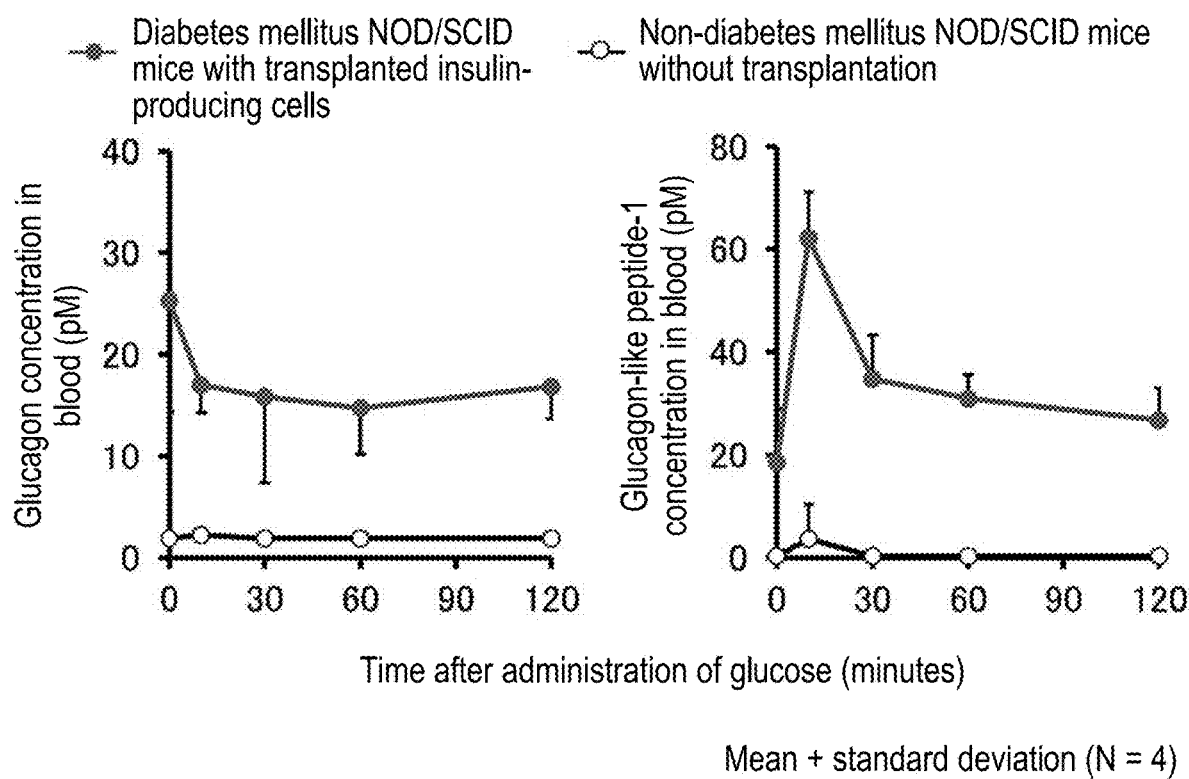
FIG. 13 shows glucagon and glucagon-like peptide-1 measured over time after glucose loading for NOD/SCID mice having an Akita gene mutation whose high blood sugar has been completely improved through transplantation of insulin-producing cells dispersed in a fibrin gel.

Test (1): FIG. 13 shows glucagon and glucagon-like peptide-1 concentrations in blood after glucose loading. Human C-peptide and glucagon-like peptide-1 concentrations in blood temporarily increased as a result of glucose loading, and glucagon concentrations in blood showed a decreasing tendency. The glucagon-like peptide-1 and glucagon concentrations in blood in mice with transplantation showed values higher than those in non-diabetes mellitus mice without transplantation, which suggested that the biological tissue-like structure released those hormones.

Figure 14:
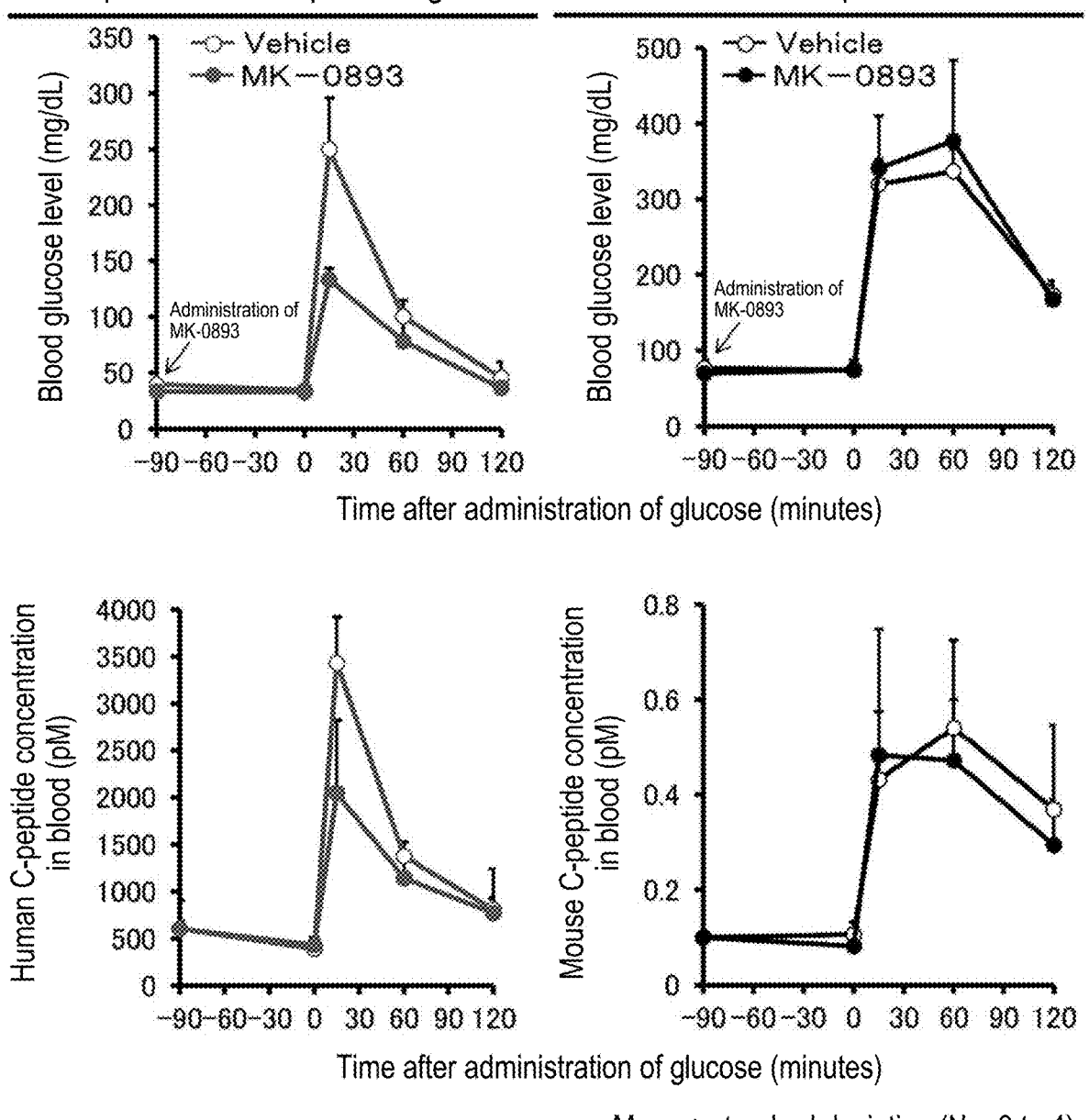
FIG. 14 shows blood glucose levels and human C-peptide concentrations in blood measured over time after treatment with the glucagon receptor antagonist MK-0893 followed by loading with glucose for STZ diabetes mellitus NOD/SCID mice whose high blood sugar has been completely improved through transplantation of insulin-producing cells dispersed in a fibrin gel.

Test (2); FIG. 14 shows blood glucose levels and human C-peptide concentrations in blood after glucose loading. Pretreatment with MK-0893 reduced temporary increase in blood glucose levels after glucose loading, and reduced increase in human C-peptide concentrations in blood, similarly. By contrast, MK-0893 did not affect blood glucose levels and endogenous mouse C-peptide concentrations in blood in non-diabetes mellitus mice without transplantation. These suggested that glucagon is involved in the blood sugar control action of the biological tissue-like structure.

Figure 15:
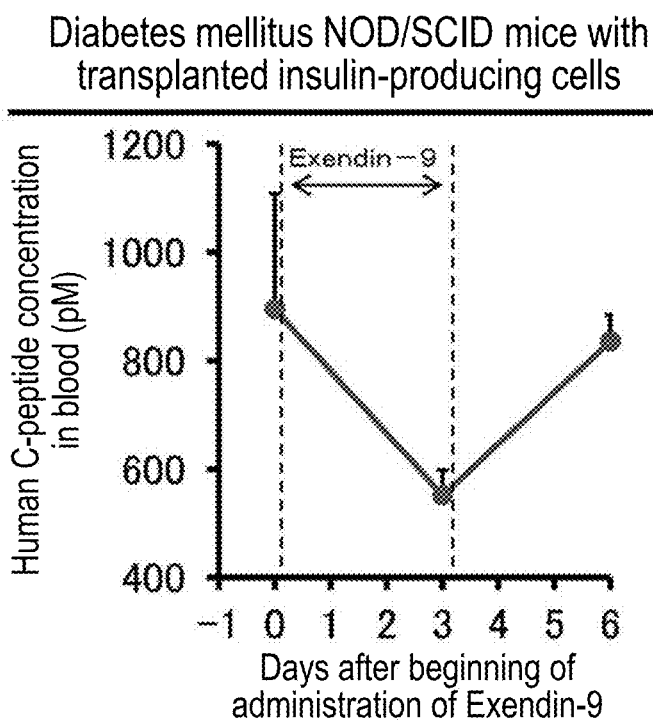
FIG. 15 shows postprandial human C-peptide concentrations in blood measured before and after treatment with the glucagon-like peptide-1 receptor antagonist Exendin-9 for 3 days for Akita diabetes mellitus NOD/SCID mice whose high blood sugar has been completely improved through transplantation of insulin-producing cells dispersed in a fibrin gel.

Test (3): FIG. 15 shows postprandial human C-peptide concentrations in blood before and after administration of Exendin-9 for 3 days. Human C-peptide concentrations in blood decreased by continuous administration of Exendin-9, and returned to the levels before administration when the administration was discontinued. It was demonstrated that the release of human C-peptide by the biological tissue-like structure is controlled by glucagon-like peptide-1.

Test (4): Human C-peptide concentrations in blood largely decreased when low blood sugar was induced by administration of glargine. These changes were similar to the transitions of endogenous mouse C-peptide concentration in blood in non-diabetes mellitus mice without transplantation. It was demonstrated that the biological tissue-like structure exhibits an insulin secretion regulation function similar to that of the endogenous pancreatic islet in inducing low blood sugar.

From the above, it was demonstrated that the biological tissue-like structure derived from insulin-producing cells formed by transplanting the fibrin gel in which the insulin-producing cells are dispersed exerts the physiological blood sugar control function in which multiple pancreatic islet hormones are involved, the function resembling that of the endogenous pancreatic islet.

The invention claimed is:

1. A composition comprising: a biocompatible material; and cells derived from human pluripotent stem cells, for use in a method for producing a biological tissue-like structure in a biological tissue of a host animal, wherein the cells derived from human pluripotent stem cells are dispersed in the biocompatible material,
   wherein the cells derived from human pluripotent stem cells are insulin-producing cells and
   wherein a proportion of Ki67-positive cells in the cells derived from human pluripotent stem cells is less than 1%.

2. The composition according to claim 1, wherein the biocompatible material is a fibrin gel.

3. The composition according to claim 2, wherein the fibrin gel is obtained by mixing the cells derived from human pluripotent stem cells with fibrinogen and thrombin for gelation immediately before use of the composition.

4. The composition according to claim 1, wherein the cells derived from human pluripotent stem cells are present in a form of a plurality of spheroids.

5. The composition according to claim 1, wherein the method comprises transplanting the composition into a biological tissue of a host animal to induce differentiation of the cells derived from human pluripotent stem cells disposed to be dispersed in the biocompatible material.

6. The composition according to claim 5, wherein the biological tissue of the host animal is a subcutaneous tissue.

7. The composition according to claim 1, wherein the biological tissue-like structure comprises:
   (a) a plurality of clusters consisting of differentiated cells obtained by inducing differentiation of the cells derived from human pluripotent stem cells;
   (b) a connective tissue derived from the host animal; and
   (c) blood vessels derived from the host animal, wherein the plurality of clusters consisting of differentiated cells are dispersed in the biological tissue-like structure, wherein the connective tissue surrounds the plurality of clusters consisting of differentiated cells, and wherein the blood vessels intrude into the plurality of clusters consisting of differentiated cells.

8. The composition according to claim 7, wherein the differentiated cells comprise no exocrine cell.

9. A biological tissue-like structure comprising:
   (a) a plurality of clusters consisting of differentiated cells obtained by inducing differentiation of cells derived from human pluripotent stem cells;
   (b) a connective tissue derived from a host animal; and
   (c) blood vessels derived from the host animal, wherein the plurality of clusters consisting of differentiated cells are dispersed in the biological tissue-like structure, wherein the connective tissue surrounds the plurality of clusters consisting of differentiated cells, and wherein the blood vessels intrude into the plurality of clusters consisting of differentiated cells.

10. The biological tissue-like structure according to claim 9, wherein the differentiated cells comprise pancreatic β cells.

11. The biological tissue-like structure according to claim 9, wherein the differentiated cells comprise no exocrine cell.

12. The biological tissue-like structure according to claim 9, used for controlling a blood glucose level of a test subject with the biological tissue-like structure transplanted thereinto to a normal level.

13. A method for producing a biological tissue-like structure, the method comprising transplanting the composition of claim 1 comprising a biocompatible material and cells derived from human pluripotent stem cells into a biological tissue of a host animal, wherein the cells derived from the human pluripotent stem cells are dispersed in the biocompatible material, and wherein the human pluripotent stem cells undergo differentiation following transplantation to create the tissue-like structure.

14. The method according to claim 13, wherein the biocompatible material is a fibrin gel.

15. The method according to claim 14, wherein the fibrin gel is obtained by mixing the cells derived from human pluripotent stem cells with fibrinogen and thrombin for gelation immediately before use of the composition.

16. The method according to claim 13, wherein the cells derived from human pluripotent stem cells are present in a form of a plurality of spheroids.

17. The method according to claim 13, wherein the cells derived from human pluripotent stem cells are insulin-producing cells.

18. The method according to claim 13, wherein the biological tissue of the host animal is a subcutaneous tissue.

19. The method according to claim 13, wherein the biological tissue-like structure comprises: a plurality of clusters consisting of differentiated cells obtained by inducing differentiation of the dispersed cells derived from human pluripotent stem cells; a connective tissue derived from the host animal; and blood vessels derived from the host animal, wherein the plurality of clusters consisting of differentiated cells is present to be dispersed in the biological tissue-like structure, the connective tissue surrounds the plurality of clusters consisting of differentiated cells, and the blood vessels are intruding into the plurality of clusters consisting of differentiated cells.

20. The method according to claim 13, wherein the differentiated cells comprise no exocrine cell.

* * * * *